（12) United States Patent
Popovic et al.

(10) Patent No.: US 10,275,567 B2
(45) Date of Patent: Apr. 30, 2019

(54) SYSTEMS AND METHODS FOR HAPLOTYPING

(71) Applicant: Seven Bridges Genomics Inc., Cambridge, MA (US)

(72) Inventors: Milos Popovic, Belgrade (RS); Goran Rakocevic, Belgrade (RS)

(73) Assignee: SEVEN BRIDGES GENOMICS INC., Cambridge, MA (US)

( * ) Notice: Subject to any disclaimer, the term of this patent is extended or adjusted under 35 U.S.C. 154(b) by 349 days.

(21) Appl. No.: 15/003,374

(22) Filed: Jan. 21, 2016

(65) Prior Publication Data
US 2016/0342732 A1    Nov. 24, 2016

Related U.S. Application Data

(60) Provisional application No. 62/165,403, filed on May 22, 2015.

(51) Int. Cl.
G01N 33/48 (2006.01)
G01N 33/50 (2006.01)
G06F 19/18 (2011.01)
C12Q 1/6827 (2018.01)
G06F 19/24 (2011.01)

(52) U.S. Cl.
CPC .......... G06F 19/18 (2013.01); C12Q 1/6827 (2013.01); G06F 19/24 (2013.01)

(58) Field of Classification Search
None
See application file for complete search history.

(56) References Cited

U.S. PATENT DOCUMENTS

| 4,683,195 A | 7/1987 | Mullis et al. |
| 4,683,202 A | 7/1987 | Mullis |
| 4,988,617 A | 1/1991 | Landegren et al. |
| 5,234,809 A | 8/1993 | Boom et al. |
| 5,242,794 A | 9/1993 | Whiteley et al. |
| 5,494,810 A | 2/1996 | Barany et al. |
| 5,583,024 A | 12/1996 | McElroy et al. |

(Continued)

FOREIGN PATENT DOCUMENTS

| KR | 101282798 B1 | 7/2013 |
| WO | 2007/086935 A2 | 8/2007 |

(Continued)

OTHER PUBLICATIONS

Norton et al. Universal, robust, highly quantitative SNP allele frequency measurement in DNA pools. Human Genetics, vol. 110, pp. 471-478. (Year: 2002).*

(Continued)

*Primary Examiner* — Russell S Negin
(74) *Attorney, Agent, or Firm* — Morgan Lewis & Bockius LLP

(57) ABSTRACT

The invention relates to methods for determining a haplotype for an organism by using a system for transforming SNP alleles found in sequence fragments into vertices in a graph with edges connecting vertices for alleles that appear together in a sequence fragment. A community detection operation can be used to infer the haplotype from the graph. The system may produce a report that includes the haplotype of the SNPs found in the genome of that organism.

23 Claims, 11 Drawing Sheets

(56) References Cited

U.S. PATENT DOCUMENTS

| | | | |
|---|---|---|---|
| 5,674,713 A | 10/1997 | McElroy et al. | |
| 5,700,673 A | 12/1997 | McElroy et al. | |
| 5,701,256 A | 12/1997 | Marr et al. | |
| 6,054,278 A | 4/2000 | Dodge et al. | |
| 6,210,891 B1 | 4/2001 | Nyren et al. | |
| 6,223,128 B1 | 4/2001 | Allex et al. | |
| 6,306,597 B1 | 10/2001 | Macevicz | |
| 6,582,938 B1 | 6/2003 | Su et al. | |
| 6,818,395 B1 | 11/2004 | Quake et al. | |
| 6,828,100 B1 | 12/2004 | Ronaghi | |
| 6,833,246 B2 | 12/2004 | Balasubramanian | |
| 6,890,763 B2 | 5/2005 | Jackowski et al. | |
| 6,911,345 B2 | 6/2005 | Quake et al. | |
| 6,925,389 B2 | 8/2005 | Hitt et al. | |
| 6,989,100 B2 | 1/2006 | Norton | |
| 7,169,560 B2 | 1/2007 | Lapidus et al. | |
| 7,232,656 B2 | 6/2007 | Balasubramanian et al. | |
| 7,282,337 B1 | 10/2007 | Harris | |
| 7,321,623 B2 | 1/2008 | Dambrackas | |
| 7,483,585 B2 | 1/2009 | Brakus, Jr. | |
| 7,598,035 B2 | 10/2009 | Macevicz | |
| 7,620,800 B2 | 11/2009 | Huppenthal et al. | |
| 7,776,616 B2 | 8/2010 | Heath et al. | |
| 7,809,509 B2 | 10/2010 | Milosavljevic | |
| 7,835,871 B2 | 11/2010 | Kain et al. | |
| 7,917,302 B2 | 3/2011 | Rognes | |
| 7,957,913 B2 | 6/2011 | Chinitz et al. | |
| 7,960,120 B2 | 6/2011 | Rigatti et al. | |
| 8,146,099 B2 | 3/2012 | Tkatch et al. | |
| 8,165,821 B2 | 4/2012 | Zhang | |
| 8,209,130 B1 | 6/2012 | Kennedy et al. | |
| 8,340,914 B2 | 12/2012 | Gatewood et al. | |
| 8,370,079 B2 | 2/2013 | Sorenson et al. | |
| 8,972,201 B2 | 3/2015 | Mande et al. | |
| 9,063,914 B2 | 6/2015 | Kural et al. | |
| 9,092,402 B2 | 7/2015 | Kural et al. | |
| 9,116,866 B2 | 8/2015 | Kural | |
| 2002/0164629 A1 | 11/2002 | Quake et al. | |
| 2002/0190663 A1 | 12/2002 | Rasmussen | |
| 2004/0023209 A1 | 2/2004 | Jonasson | |
| 2004/0243982 A1* | 12/2004 | Robison | G06F 8/443 717/132 |
| 2005/0089906 A1 | 4/2005 | Furuta et al. | |
| 2006/0024681 A1 | 2/2006 | Smith et al. | |
| 2006/0195269 A1 | 8/2006 | Yeatman et al. | |
| 2006/0292611 A1 | 12/2006 | Berka et al. | |
| 2007/0114362 A1 | 5/2007 | Feng et al. | |
| 2007/0166707 A1 | 7/2007 | Schadt et al. | |
| 2008/0003571 A1 | 1/2008 | McKernan et al. | |
| 2008/0251711 A1 | 10/2008 | Reilly | |
| 2008/0281463 A1 | 11/2008 | Suh et al. | |
| 2008/0294403 A1 | 11/2008 | Zhu et al. | |
| 2009/0026082 A1 | 1/2009 | Rothberg et al. | |
| 2009/0119313 A1 | 5/2009 | Pearce | |
| 2009/0127589 A1 | 5/2009 | Rothberg et al. | |
| 2009/0191565 A1 | 7/2009 | Lapidus et al. | |
| 2009/0233809 A1 | 9/2009 | Faham et al. | |
| 2009/0300781 A1 | 12/2009 | Bancroft et al. | |
| 2009/0318310 A1 | 12/2009 | Liu et al. | |
| 2009/0325145 A1 | 12/2009 | Sablon et al. | |
| 2010/0010992 A1 | 1/2010 | Morris | |
| 2010/0035252 A1 | 2/2010 | Rothberg et al. | |
| 2010/0137143 A1 | 6/2010 | Rothberg et al. | |
| 2010/0169026 A1 | 7/2010 | Sorenson et al. | |
| 2010/0188073 A1 | 7/2010 | Rothberg et al. | |
| 2010/0197507 A1 | 8/2010 | Rothberg et al. | |
| 2010/0240046 A1 | 9/2010 | Palmer et al. | |
| 2010/0282617 A1 | 11/2010 | Rothberg et al. | |
| 2010/0285578 A1 | 11/2010 | Selden et al. | |
| 2010/0300559 A1 | 12/2010 | Schultz et al. | |
| 2010/0300895 A1 | 12/2010 | Nobile et al. | |
| 2010/0301398 A1 | 12/2010 | Rothberg et al. | |
| 2010/0304982 A1 | 12/2010 | Hinz et al. | |
| 2011/0004413 A1 | 1/2011 | Carnevali et al. | |
| 2011/0009278 A1 | 1/2011 | Kain et al. | |
| 2011/0098193 A1 | 4/2011 | Kingsmore et al. | |
| 2011/0207135 A1 | 8/2011 | Faham et al. | |
| 2011/0257889 A1 | 10/2011 | Klammer et al. | |
| 2012/0030566 A1 | 2/2012 | Victor | |
| 2012/0040851 A1 | 2/2012 | Lieberman et al. | |
| 2012/0041727 A1 | 2/2012 | Mishra et al. | |
| 2012/0157322 A1 | 6/2012 | Myllykangas et al. | |
| 2012/0239706 A1 | 9/2012 | Steinfadt | |
| 2012/0330566 A1 | 12/2012 | Chaisson | |
| 2013/0029879 A1 | 1/2013 | Shetty et al. | |
| 2013/0035904 A1 | 2/2013 | Kuhn | |
| 2013/0059740 A1 | 3/2013 | Drmanac et al. | |
| 2013/0073214 A1 | 3/2013 | Hyland et al. | |
| 2013/0096178 A1* | 4/2013 | Ralston | C12Q 1/6883 514/44 A |
| 2013/0124100 A1 | 5/2013 | Drmanac et al. | |
| 2013/0232480 A1 | 9/2013 | Winterfeldt et al. | |
| 2013/0311106 A1 | 11/2013 | White et al. | |
| 2013/0332081 A1 | 12/2013 | Reese et al. | |
| 2013/0345066 A1 | 12/2013 | Brinza et al. | |
| 2014/0012866 A1 | 1/2014 | Bowman et al. | |
| 2014/0051588 A9 | 2/2014 | Drmanac et al. | |
| 2014/0129201 A1 | 5/2014 | Kennedy et al. | |
| 2014/0136120 A1 | 5/2014 | Colwell et al. | |
| 2014/0200147 A1 | 7/2014 | Bartha et al. | |
| 2014/0278590 A1 | 9/2014 | Abbassi et al. | |
| 2014/0280360 A1 | 9/2014 | Webber et al. | |
| 2014/0281708 A1 | 9/2014 | Adam et al. | |
| 2015/0020061 A1 | 1/2015 | Ravi | |
| 2015/0056613 A1 | 2/2015 | Kural | |
| 2015/0057946 A1 | 2/2015 | Kural | |
| 2015/0066383 A1 | 3/2015 | Wernicke | |
| 2015/0112602 A1 | 4/2015 | Kural et al. | |
| 2015/0112658 A1 | 4/2015 | Kural et al. | |

FOREIGN PATENT DOCUMENTS

| | | |
|---|---|---|
| WO | 2010/010992 A1 | 1/2010 |
| WO | 2012/098515 A1 | 7/2012 |
| WO | 2012/142531 A2 | 10/2012 |
| WO | 2013/035904 A1 | 3/2013 |

OTHER PUBLICATIONS

Waterman, 1976, Some biological sequence metrics, Adv Math 20(3):367-387.

Wellcome Trust Case Control Consortium, 2007, Genome-wide association study of 14,000 cases of seven common diseases and 3,000 shared controls, Nature 447:661-678.

Wu, 2010, Fast and SNP-tolerant detection of complex variants and splicing in short reads, Bioinformatics, 26(7):873-881.

Xing, 2006, An expectation-maximization algorithm for probabilistic reconstructions of full-length isoforms from splice graphs, Nucleic Acids Research, 34:3150-3160.

Yanovsky, 2008, Read mapping algorithms for single molecule sequencing data, Proc 8th Int Workshop Alg Bioinformatics 5251:38-49.

Yu, 2010, The construction of a tetraploid cotton genome wide comprehensive reference map, Genomics 95:230-240.

International Search Report and Written Opinion dated Jan. 5, 2016, for International Patent Application No. PCT/US2015/054461 with International Filing Date Oct. 7, 2015 (7 pages).

International Search Report and Written Opinion dated Mar. 19, 2015, for International Patent Application No. PCT/US2014/061162 with International Filing Date Oct. 17, 2014 (12 pages).

International Search Report and Written Opinion dated May 11, 2015, for International Patent Application No. PCT/US2015/015375 with International Filing Date Feb. 11, 2015 (12 pages).

International Search Report and Written Opinion dated May 5, 2016, for International Patent Application No. PCT/US2016/020899, wiht International Filing Date Mar. 4, 2016 (12 pages).

International Search Report and Written Opinion dated Dec. 11, 2014, for International Patent Application No. PCT/US14/52065, filed Aug. 21, 2014, (18 pages).

(56) References Cited

OTHER PUBLICATIONS

International Search Report and Written Opinion dated Dec. 30, 2014, for International Patent Application No. PCT/US14/58328, filed Sep. 30, 2014 (22 pages).
International Search Report and Written Opinion dated Feb. 4, 2015, for Patent Application No. PCT/US2014/061158, filed Oct. 17, 2014, (11 pages).
International Search Report and Written Opinion dated Jan. 27, 2015, for International Patent Application No. PCT/US2014/060680, filed Oct. 215, 2014, (11 pages).
International Search Report and Written Opinion dated Sep. 2, 2016, for International Patent Application No. PCT/US2016/033201 with International Filing Date May 19, 2016 (14 pages).
International Search Report and Written Opinion dated Sep. 7, 2016, for International Application No. PCT/US2016/036873 with International filing date Jun. 10, 2016 (8 pages).
International Search Report and Written Opinion of the International Searching Authority dated Nov. 17, 2015 for International Application No. PCT/US2015/048891 (11 Pages).
Katoh, 2005, MAFFT version 5: improvement in accuracy of multiple sequence alignment, Nucl Acids Res 33(2):511-518.
Kehr, 2014, Genome alignment with graph data structures: a comparison, BMC Bioinformatics 15:99.
Kent, 2002, BLAT—The Blast-Like Alignment Tool, Genome Research 4:656-664.
Kim, 2005, ECgene: Genome-based EST clustering and gene modeling for alternative splicing, Genome Res 15:566-576.
Kim, 2008, A Scaffold Analysis Tool Using Mate-Pair Information in Genome Sequencing, Journal of Biomedicine and Biotechnology 8(3):195-197.
Kim, 2013, TopHat2: accurate alignment of transcriptomes in the presence of insertions, deletions and gene fusions, Genome Biol 14(4):R36.
Kurtz, 2004, Versatile and open software for comparing large genomes, Genome Biol 5:R12.
LaFramboise, 2009, Single nucleotide polymorphism arrays: a decade of biological, computational and technological advance, Nucleic Acids Res 37(13):4181-4193.
Lam, 2008, Compressed indexing and local alignment of DNA, Bioinformatics 24(6):791-97.
Langmead, 2009, Ultrafast and memory-efficient alignment of short DNA sequences to the human genome, Genome Biol 10:R25.
Larkin, 2007, Clustal W and Clustal X version 2.0, Bioinformatics 23(21):2947-2948.
Layer, 2015, Efficient compression and analysis of large genetic variation datasets, Biorxiv preprint, available at http://biorxiv.org/content/early/2015/04/20/018259.
Layer, 2015, Efficient genotype compression and analysis of large genetic-variation data sets, Nat Meth 13(1):63-65.
Lee, 2002, Multiple sequence alignment using partial order graphs, Bioinformatics 18(3):452-464.
Lee, 2003, Generating consensus sequences from partial order multiple sequence alignment graphs, Bioinformatics 19(8):999-1008.
Lee, 2005, Bioinformatics analysis of alternative splicing, Brief Bioinf 6(1):23-33.
Lee, 2014, MOSAIK: A hash-based algorithm for accurate next-generation sequencing short-read mapping, PLoS One 9(3):e90581.
LeGault 2010, Learning Probalistic Splice Graphs from RNA-Seq data, pages.cs.wisc.edu/~legault/cs760_writeup.pdf; retrieved from the Internet on Apr. 6, 2014.
LeGault, 2013, Inference of alternative splicing from RNA-Seq data with probabilistic splice graphs, Bioinformatics 29(18):2300-2310.
Leipzig, 2004, The alternative splicing gallery (ASG): Bridging the gap between genome and transcriptome, Nuc Acids Res 23(13):3977-3983.
Li, 2008, SOAP: short oligonucleotide alignment program, Bioinformatics 24(5):713-14.
Li, 2009, SOAP2: an improved ultrafast tool for short read alignment, Bioinformatics 25(15):1966-67.
Li, 2010, A survey of sequence alignment algorithms for next-generation sequencing, Briefings in Bionformatics 11(5):473-483.
Li, 2015, BGT: efficient and flexible genotype query across many samples, arXiv:1506.08452 [q-bio.GN].
Li, 2015, Towards Better Understanding of Artificats in Variant Calling from High-Coverage Samples, arXiv:1404.0929 [q-bio.GN].
Life Technologies, 2013, Rapid Exome Sequencing Using the Ion Proton System and Ion Ampliseq Technology, Application Note (5 Pages).
Lindgreen, 2012, AdapterRemoval: easy cleaning of next-generation sequence reads, BMC Res Notes 5:337.
Lipman, 1985, Rapid and sensitive protein similarity searches, Science 227(4693):1435-41.
Lucking 2011, PICS-Ord: unlimited coding of ambiguous regions by pairwise identity and cost scores ordination, BMC Bioinf 12:10.
Ma, 2010, Multiple genome alignment based on longest path in directed acyclic graphs, Int J Bioinformatics 6(4):366-683, summary only.
Machine translation of KR 10-1282798 B1 generated on Jan. 6, 2016, by the website of the European Patent Office (23 pages).
Mamoulis, 2004, Non-contiguous sequence pattern queries, in Advances in Database Technology—EDBT 2004: 9th International Conference on Extending Database Technology, Heraklion, Crete, Greece, Mar. 14-18, 2004, Proceedings (18 pages); retreived from the internet on Jun. 3, 2016, at <http://Lcs.hku.hk/~nikos/seqjoin.pdf>.
Manolio, 2010, Genome wide association studies and assessment of the risk of disease, NEJM 363(2):166-76.
Mardis, 2010, The $1,000 genome, the $100,000 analysis?, Genome Med 2:84-85.
Margulies, 2005, Genome sequencing in micro-fabricated high-density picotiter reactors, Nature 437:376-380.
McSherry, 2001, Spectral partitioning of random graphs, Proc 42nd IEEE Symp Found Comp Sci 529-537.
Miller, 2010, Assembly Algorithms for Next-Generation Sequencing Data, Genomics 95(6):315-327.
Misra, 2011, Anatomy of a hash-based long read sequence mapping algorithm for next generation DNA sequencing, Bioinformatics 27(2):189-195.
Moudrianakis, 1965, Base sequence determination in nucleic acids with electron microscope III: chemistry and microscopy of guanine-labelled DNA, PNAS 53:564-71.
Mount, 2001, Multiple Sequence Alignment, Bioinformatics, 2001, Cold Spring Harbor Laboratory Press, Cold Spring Harbor, New York, pp. 139-204.
Nagalakshmi, 2010, RNA-Seq: A Method for Comprehensive Transcriptome Analysis, Curr Proc Mol Biol 4.11.1.13.
Nagarajan, 2013, Sequence assembly demystified, Nat Rev 14:157-167.
Najafi, 2016, Fundamental limits of pooled-DNA sequencing, arXiv:1604.04735.
Nakao, 2005, Large-scale analysis of human alternative protein isoforms: pattern classification and correlation with subcellular localization signals, Nucl Ac Res 33(8):2355-2363.
Needleman, 1970, A general method applicable to the search for similarities in the amino acid sequence of two proteins, J Mol Biol 48(3):443-453.
O'Rawe, 2013, Low Concordance of Multiple Variant-Calling Pipelines: Practical Implications for Exome and Genome Sequencing, Genome Med 5:28.
Oshlack, 2010, From RNA-seq reads to differential expression results. Genome Bio 11:220.
Pe'er, 2006, Evaluating and improving power in whole-genome association studies using fixed marker sets. Nat Genet 38:663-667.
Pearson, 1988, Improved tools for biological sequence comparison, PNAS 85(8):2444-8.
Pope, 2014, ROVER Variant Caller: Read-Pair Overlap Considerate Variant-Calling Software Applied to PCR-Based Massively Parallel Sequencing Datasets, Source Code Bio Med 9:3.
Popitsch, 2013, NGC: lossless and lossy compression of aligned high-throughput sequencing data, Nucl Acids Res, 41(1):e27.
Potter, 1994, ASC: An Associative-Computing Paradigm, Computer 27(11):19-25.

(56) References Cited

OTHER PUBLICATIONS

Quail, et al., 2012, A tale of three next generation sequencing platforms: comparison of Ion Torrent, Pacific Biosciences and Illumina MiSeq sequencers, BMC Genomics 13:341.
Rajaram, 2013, Pearl millet [Pennisetum glaucum (L.) R. Br.] consensus linkage map constructed using four RIL mapping populations and newly developed EST-SSRs, BMC Genomics 14(1):159.
Ramirez-Gonzalez, 2011, Gee Fu: a sequence version and web-services database tool for genomic assembly, genome feature and NGS data, Bioinformatics 27(19):2754-2755.
Raphael, 2004, A novel method for multiple alignment of sequences with repeated and shuffled elements, Genome Res 14:2336-2346.
Rodelsperger, 2008, Syntenator: Multiple gene order alignments with a gene-specific scoring function, Alg Mol Biol 3:14.
Rognes, 2000, Six-fold speed-up of Smith-Waterman sequence database searching using parallel processing on common microprocessors, Bioinformatics 16(8):699-706.
Rognes, 2001, ParAlign: a parallel sequence alignment algorithm for rapid and sensitive database searches, Nucl Ac Res 29(7):1647-1652.
Rognes, 2011, Faster Smith-Waterman database searches with inter-sequence SIMD parallelisation, Bioinformatics 12:221.
Rothberg, 2011, An integrated semiconductor device enabling non-optical genome sequencing, Nature 475:348-352.
Saebo, 2005, PARALIGN: rapid and sensitive sequence similarity searches powered by parallel computing technology, Nucl Ac Res 33:W535-W539.
Sato, 2008, Directed acyclic graph kernels for structural RNA analysis, BMC (BioMed Central) Bioinformatics 9(318).
Schneeberger, 2009, Sumaltaneous alignment of short reads against multiple genomes, Genome Biol 10(9):R98.2-R98.12.
Schwikowski, 2002, Weighted sequence graphs: boosting iterated dynamic programming using locally suboptimal solutions, Disc Appl Mat 127:95-117.
Shao, 2006, Bioinformatic analysis of exon repetition, exon scrambling and trans-splicing in humans, Bioinformatics 22: 692-698.
Sievers, 2011, Fast, scalable generation of high-quality protein multiple sequence alignments using Clustal Omeag, Mol Syst Biol 7:539.
Slater, 2005, Automated generation of heuristics for biological sequence comparison, BMC Bioinformatics 6:31.
Smith, 1981, Identification of common molecular subsequences, J Mol Biol, 147(1):195-197.
Smith, 2012, Multiple insert size paired-end sequencing for deconvolution of complex transcriptions, RNA Bio 9(5) 596-609.
Soni, 2007, Progress toward ultrafast DNA sequencing using solid-state nanopores, Clin Chem 53(11):1996-2001.
Sosa, 2012, Next-Generation Sequencing of Human Mitochondrial Reference Genomes Uncovers High Heteroplasmy Frequency, PLoS One 8(10):e1002737.
Stephens, 2001, A new statistical method for haplotype reconstruction from population data, Am J Hum Genet 68:978-989.
Stewart, 2011, A comprehensive map of mobile element insertion polymorphisms in humans, PLoS Genetics 7(8):1-19.
Subramanian, 2008, DIALIGN-TX: greedy and progessive approaches for segment-based multiple sequence alignment, Alg Mol Biol 3(1):1-11.
Sudmant, 2015, An integrated map of structural variation in 2,504 human genomes, Nature 526:75-81.
Sun, 2006, Pairwise Comparison Between Genomic Sequences and Optical maps, dissertation, New York University (131 pages); retreived from the internet on Jun. 3, 2016, at <https://cs.nyu.edu/mishra/PEOPLE/sun_bing.pdf>.
Szalkowski, 2012, Fast and robust multiple sequence alignment with phylogeny-aware gap placement, BMC (BioMed Central) Bioinformatics 13(129).
Szalkowski, 2013, Graph-based modeling of tandem repeats improves global multiple sequence alignment, Nucl Ac Res 41(17):e162.
Tarhio, 1993, Approximate Boyer-Moore String Matching, SIAM J Comput 22(2):243-260.
Tewhey, 2011, The importance of phase information for human genomics, Nat Rev Gen 12:215-223.
The 1000 Genomes Project, 2015, A global reference for human genetic variation, Nature 526:68-74.
The Variant Call Format (VCF) Version 4.2 Specification (Jan. 26, 2015), available at https://samtools.github.io/hts-specs/VCFv4.2.pdf.
Thomas, 2014, Community-wide effort aims to better represent variation in human reference genome, Genome Web (11 pages).
Trapnell, 2010, Transcript assembly and abundance estimation from RNA-Seq reveals thousands of new transcripts and switching among isoforms, Nat Biotech 28(5):511-515.
Trapnell, 2010, Transcript assembly and quantification by RNA-Seq reveals unannotated trancripts and isoform switching during cell differentiation, Nat Biotech 28(5):511-515.
Wallace, 2005, Multiple sequence alignments, Curr Op Struct Biol 15(3):261-266.
Wang, 2009, RNA-Seq: a revolutionary tool for transcriptomics, Nat Rev Genet 10(1):57-63.
Wang, 2011, Next generation sequencing has lower sequence coverage and poorer SNP-detection capability in the regulatory regions, Scientific Reports 1:55.
Aguiar and Istrail, 2012, HapCompass: A fast cycle basis algorithm for accurate haplotype assembly of sequence data, J Comp Biol 19(6):577-590.
Airoldi et al, 2008, Mixed membership stochastic blockmodels, JMLR 9:1981-2014.
Bansal et al., 2008, An MCMC algorithm for haplotype assembly from whole-genome sequence data, Genome Research 18:1336-1346.
Clark, 2014, Illumina announces landmark $1,000 human genome sequencing, Wired, Jan. 15, 2014.
Danecek et al., 2011, The variant call format and VCFtools, Bioinformatics 27(15):2156-2158.
Glusman et al., 2014, Whole-genome haplotyping approaches and genomic medicine, Genome Medicine 6:73.
Harenberg, 2014, Community detection in large-scale networks: a survey and empirical evaluation, WIREs Comp Stat 6:426-439.
He et al. 2010, Optimal algorithms for haplotype assembly from whole-genome sequence data, Bioinformatics 26: i183-i190.
Li & Durbin, 2009, Fast and accurate short read alignment with Burrows-Wheeler Transform. Bioinformatics 25:1754-60.
Li et al., 2009, The Sequence Alignment/Map format and SAMtools, Bioinformatics 25(16):2078-9.
Mazrouee & Wang, 2014, FastHap: fast and accurate single individual haplotype reconstructions using fuzzy conflict graphs, Bioinformatics 30:i371-i378.
McKenna et al., 2010, The Genome Analysis Toolkit: a MapReduce framework for analyzing next-generation DNA sequencing data, Genome Res 20(9):1297-1303.
Newman, 2013, Community detection and graph portioning, Europhys Lett 103(2):28003, arXiv:1305.4974v1.
Ning et al., 2001, SSAHA: a fast search method for large DNA databases, Genome Research 11(10):1725-9.
Pearson & Lipman, 1988, Improved tools for biological sequence comparison, PNAS 85:2444-2448.
Peixoto, 2014, Efficient Monte Carlo and greedy heuristic for the inference of stochastic block models, Phys. Rev. E 89, 012804.
Yang, 2013, Leveraging reads that span multiple single nucleotide polymorphisms for haplotype inference from sequencing data, Bioinformatics 29(18):2245-2252.
Yang, 2014, Community detection in networks with node attributes, proc IEEE ICDM '13, arXiv:1401.7267.
Durham, et al., EGene: a configurable pipeline system for automated sequence analysis, Bioinformatics 21(12):2812-2813 (2005).
Yu, et al., A tool for creating and parallelizing bioinformatics pipelines, DOD High Performance Computing Conf., 417-420 (2007).
Hoon, et al., Biopipe: A flexible framework for protocol-based bioinformatics analysis, Genome Research 13(8):1904-1915 (2003).
Abouelhoda et al., 2012, Tavaxy: integrating Tavema and Galaxy workflows with cloud computing support, BMC Bioinformatics 13:77.

(56) References Cited

OTHER PUBLICATIONS

Cohen-Boulakia et al., 2014, Distilling structure in Taverna scientific workflows: a refactoring approach, BMC Bioinformatics 15(Suppl 1):S12.
Hull et al., 2006, Taverna: a tool for building and running workflows of services, Nucl Acids Res 34(Web Server issue): W729-32.
Kano et al., 2010, Text mining meets workflow: linking U-Compare with Tavema, Bioinformatics 26(19):2486-7.
Kawas et al., 2006, BioMoby extensions to the Taverna workflow management and enactment software, BMC Bioinformatics 7:523.
Krabbenhöft et al., 2008, Integrating ARC grid middleware with Taverna workflows, Bioinformatics 24(9):1221-2.
Kuhn et al., 2010, CDK-Taverna: an open workflow environment for cheminformatics, BMC Bioinformatics 11:159.
Lanzén et al., 2008, The Taverna Interaction Service: enabling manual interaction in workflows, Bioinformatics 24(8):1118-20.
Li et al., 2008, Automated manipulation of systems biology models using libSBML within Taverna workflows, Bioinformatics 24(2):287-9.
Li et al., 2008, Performing statistical analyses on quantitative data in Taverna workflows: an example using R and maxdBrowse to identify differentially-expressed genes from microarray data, BMC Bioinformatics 9:334.
Missier et al., 2010, Taverna, reloaded, Proc. Scientific and Statistical Database Management, 22nd Int Conf, Heidelberg, Germany, Jun./Jul. 2010, Gertz & Ludascher, Eds., Springer.
Nenadic, 2010, Nested Workflows, The Tavema Knowledge Blog, Dec. 13, 2010. Retrieved on Feb. 25, 2016 from http://taverna.knowledgeblog.org/2010/12/13/nested-workflows/.
Oinn et al., 2004, Taverna: a tool for the composition and enactment of bioinformatics workflows, Bioinformatics 20(17):3045-54.
Oinn et al., 2006, Taverna: lessons in creating a workflow environment for the life sciences, Concurrency and Computation: Practice and Experience 18(10):1067-1100.
Paterson & Law, 2009, An XML transfer schema for exchange of genomic and genetic mapping data: implementation as a web service in a Taverna workflow, BMC Bioinformatics 10:252.
Sroka et al., 2006, XQTav: an XQuery processor for Taverna environment, Bioinformatics 22(10):1280-1.
Sroka et al., 2010, A formal semantics for the Taverna 2 workflow model, J Comp Sys Sci 76(6):490-508.
Sroka et al., 2011, CalcTav—integration of a spreadsheet and Taverna workbench, Bioinformatics 27(18):2618-9.
Tan et al., 2010, A Comparison of Using Taverna and BPEL in Building Scientific Workflows: the case of caGrid, Concurr Comput 22(9):1098-1117.
Tan et al., 2010, CaGrid Workflow Toolkit: a Taverna based workflow tool for cancer grid, BMC Bioinformatics 11:542.
Truszkowski et al., 2011, New developments on the cheminformatics open workflow environment CDK-Taverna, J Cheminform 3:54.
Turi et al., 2007, Taverna Workflows: Syntax and Semantics, in IEEE Int Conf on e-Science and Grid Computing, pp. 441-448.
Wassink et al., 2009, Using R in Taverna: RShell v1.2. BMC Res Notes 2:138.
Wolstencroft et al., 2005, Panoply of Utilities in Taverna, Proc 2005 First International Conference on e-Science and Grid Computing, pp. 156-162.
Wolstencroft et al., 2013, The Taverna Workflow Suite: Designing and Executing Workflows of Web Services on the Desktop, Web or in the Cloud, Nucl Acids Res 41(W1):W556-W561.
Yildiz et al., 2014, BIFI: a Taverna plugin for a simplified and user-friendly workflow platform, BMC Res Notes 7:740.
Zhang et al., 2013, Taverna Mobile: Tavema workflows on Android, EMBnet J 19(B):43-45.
Zhao et al., 2012, Why Workflows Break-Understanding and Combating Decay in Taverna Workflows, eScience 2012, Chicago, Oct. 2012.
DePristo, et al., 2011, A framework for variation discovery and genotyping using next-generation DNA sequencing data, Nature Genetics 43:491-498.
Dinov et al., 2011, Applications of the pipeline environment for visual informatics and genomic computations, BMC Bioinformatics 12:304.
Dudley and Butte, 2009, A quick guide for developing effective bioinformatics programming skills, PLoS Comput Biol 5(12):e1000589.
Durham et al., 2005, EGene: a configurable pipeline system for automated sequence analysis, Bioinformatics 21(12):2812-2813.
Goto et al., 2010, BioRuby: bioinformatics software for the Ruby programming language, Bioinformatics 26(20):2617-2619.
Holland et al., 2008, BioJava: an open-source framework for bioinformatics, Bioinformatics 24(18):2096-2097.
Hoon et al., 2003, Biopipe: A flexible framework for protocol-based bioinformatics analysis, Genome Research 13(8):1904-1915.
Kumar et al., 2010, Comparing de novo assemblers for 454 transcriptome data, BMC Genomics 11:571.
Machine translation produced on Jun. 1, 2015, by Espacenet of WO 2010/010992 A1 (11 pages).
Machine translation produced on Jun. 1, 2015, by WPIO website of WO 2013/035904 (10 pages).
Margulies et al., 2005, Genome sequencing in microfabricated high-density picolitre reactors, Nature 437:376-380.
McKenna, et al., 2010, The Genome Analysis Toolkit: a MapReduce framework for analyzing next-generation DNA sequencing data, Genome Res 20:1297-303.
Pabinger et al., 2013, A survey of tools for variant analysis of next-generation genome sequencing data, Brief Bioinf.
Posada and Crandall, 1998, Model Test: testing the model of DNA substitution, Bioinformatics 14(9):817-8.
Potter et al., 2004, The ensemble analysis pipeline, Genome Res 14:934-941.
Robertson et al., 2010, De novo assembly and analysis of RNA-seq data, Nat Meth 7(11):909.
Ronquist, et al., 2012, MrBayes 3.2: efficient Bayesian phylogenetic inference and model choice across a large model space, Syst Biol 61(3):539-42.
Schenk et al., 2013, A pipeline for comprehensive and automated processing of electron diffraction data in IPLT, J Struct Biol 182(2):173-185.
Torri et al., 2012, Next generation sequence analysis and computational genomics using graphical pipeline workflows, Genes (Basel) 3(3):545-575.
Trapnell et al., 2009, TopHat: discovering splice junctions with RNA-Seq, Bioinformatics 25:1105-1111.
Yu et al., 2007, A tool for creating and parallelizing bioinformatics pipelines, DOD High Performance Computing Conf., 417-420.
Agarwal, 2013, SINNET: Social Interaction Network Extractor from Text, Proc IJCNLP 33-36.
Aguiar, 2013, Haplotype assembly in polyploid genomes and identical by descent shared tracts, BioInformatics 29(13): i352-i360.
Altera, 2007, Implementation of the Smith-Waterman algorithm on reconfigurable supercomputing platform, White Paper ver 1.0 (18 pages).
Altschul, 1986, Optimal Sequence Alignment Using Affine Gap Costs, Bull Math Biol 48(5/6):603-616.
Bao, 2013, BRANCH: boosting RNA-Seq assemblies with partial or related genomic sequences, Bioinformatics 29(10):1250-1259.
BCF2 Quick Reference (r198), available at http://samtools.github.io/hts-specs/BCFv2_qref.pdf.
Berlin, 2014, Assembling large genomes with single-molecule sequencing and locality sensitive hashing, bioRxiv preprint (35 pages); retrieved from the internet on Jan. 29, 2015, at <http://biorxiv.org/content/biorxiv/early/2014/08/14/008003.full.pdf>.
Bertone, 2004, Global identification of human transcribed sequences with genome tiling arrays, Science 306:2242-2246.
Bertrand, 2009, Genetic map refinement using a comparative genomic approach, J Comp Biol 16(10):1475-1486.
Black, 2005, A simple answer for a splicing conundrum, PNAS 102:4927-8.
Boyer, 1977, A Fast String Searching Algorithm, Comm ACM 20(10):762-772.
Buhler, 2001, Search algorithms for biosequences using random projection, dissertation, University of Washington (203 pages);

(56) References Cited

OTHER PUBLICATIONS retreived from the internet on Jun. 3, 2016, at <http://www.mathcs.emory.edu/~cheung/papers/Matching/Search-Alg-for-Biosequences-Thesis.pdf>.
Carrington, 1985, Polypeptide ligation occurs during post-translational modification of concanavalin A, Nature 313:64-67.
Chang, 2005, The application of alternative splicing graphs in quantitative analysis of alternative splicing form from EST database, Int J Comp Appl Tech 22(1):14.
Chen, 2012, Transient hypermutability, chromothripsis and replication-based mechanisms in the generation of concurrent clustered mutations, Mutation Res 750(1):562-59.
Chin, 2013, Nonhybrid finished microbial genome assemblies from long-read SMRT sequencing data, Nat Meth 10(6):563-569.
Chuang, 2001, Gene recognition based on DAG shortest paths, Bioinformatics 17(Suppl. 1):s56-s64.
Cock, 2013, Galaxy tools and workflows for sequence analysis with applications in molecular plant pathology, Peer J 1: e167.
Compeau, 2011, How to apply de Bruijn graphs to genome assembly, Nat Biotech 29(11):987-991.
Costa, 2010, Uncovering the Complexity of Transcriptomes with RNA-Seq, J Biomed Biotech 853916.
Delcher, 1999, Alignment of whole genomes, Nucl. Acids Res 27(11):2369-76.
Durbin, 2014, Efficient haplotype matching and storage using the positional Burrows-Wheeler transform (PBWT), Bioinformatics 30(9):1266-1272.
Enedelman, 2011, New algorithm improves fine structure of the barley consensus SNP map, BMC Genomics 12(1):407 (and whole document).
Farrar, 2007, Striped Smith-Waterman speeds database searches six times over other SIMD implementations, Bioinformatics 23(2):156-161.
Fiers, 2008, High-throughput Bioinformatics with the Cyrille2 Pipeline System, BMC Bioinformatics 9:96.
Fitch, 1970, Distinguishing homologous from analogous proteins, Systematic Zoology 19:99-113.
Flicek, 2009, Sense from sequence reads: methods for alignment and assembly, Nat Meth Suppl 6(11s):s6-s12.
Florea, 2005, Gene and alternative splicing annotation with AIR, Genome Res 15:54-66.
Florea, 2013, Genome-guided transcriptome assembly in the age of next-generation sequencing, IEEE/ACM Trans Comp Biol Bioinf 10(5):1234-1240.
Garber, 2011, Computational methods for transcriptome annotation and quantification using RNA-Seq, Nat Meth 8(6):469-477.
Gotoh, 1982, An Improved Algorithm for Matching Biological Sequences, J Mol Biol 162:705-708.
Gotoh, 1999, Multiple sequence alignment: algorithms and applications, Adv Biophys 36:159-206.
Grabherr, 2011, Full-length transcriptome assembly from RNA-Seq data without a reference genome, Nat Biotech 29(7):644-654.
Guttman, 2010, Ab initio reconstruction of cell type-specific transcriptomes in mouse reveals the conserved multi-exonic structure of lincRNAs, Nat Biotech 28(5):503-510.
Guttman, 2010, Ab initio reconstruction of transcriptomes of pluripotent and lineage committed cells reveals gene structures of thousands of lincRNAs, NIH-PA Author Manuscript.
Haas, 2004, DAGchainer: a tool for mining segmental genome duplications and synteny, Bioinformatics 20(18):3643-3646.
Harrow, 2012, GENCODE: The reference human genome annotation for the ENCODE Project, Genome Res 22:1760-1774.
Heber, 2002, Splicing graphs and EST assembly problems, Bioinformatics 18 Suppl:181-188.
Hein, 1989, A new method that simultaneously aligns and reconstructs ancestral sequences for any number of homologous sequences when the phylogeny is given, Mol Biol Evol 6(6):649-668.
Hein, 1989, A tree reconstruction method that is economical in the number of pairwise comparisons used, Mol Biol Evol 6(6):649-668.
Hokamp, 2003, Wrapping up BLAST and Other Applications for Use on Unix Clusters, Bioinformatics 19(3)441-42.
Homer, 2010, Improved variant discovery through local re-alignment of short-read next generation sequencing data using SRMA, Genome Biol 11(10):R99.
Horspool, 1980, Practical Fast Searching in Strings, Software—Practice & Experience 10:501-506.
Huang, Chapter 3: Bio-Sequence Comparison and Alignment, ser. Curr Top Comp Mol Biol. Cambridge, Mass.: The MIT Press, 2002.
Hutchinson, 2014, Allele-specific methylation occurs at genetic variants associated with complex diseases, PLoS One 9(6):e98464.
International HapMap Consortium, 2005, A haplotype map of the human genome. Nature 437:1299-1320.
International Preliminary Report on Patentability issued in application No. PCT/US2014/052065 dated Feb. 23, 2016.
International Search Report and Written Opinion dated Mar. 31, 2015 for International Application No. PCT/US2015/010604 filed Jan. 8, 2015 (13 pages).
International Search Report and Written Opinion dated Dec. 30, 2014, for PCT/US14/58328, with International Filing Date Sep. 30, 2014 (15 pages).
International Search Report and Written Opinion dated Feb. 17, 2015, for International Patent Application No. PCT/US2014/061156, filed Oct. 17, 2014 (19 pages).

\* cited by examiner $P(G|B1) > P(G|B2)$

SYSTEMS AND METHODS FOR HAPLOTYPING

CROSS-REFERENCE TO RELATED APPLICATIONS

This application claims priority to and the benefit of U.S. Provisional Patent Application Ser. No. 62/165,403 for "Systems and Methods for Haplotyping", filed May 22, 2015, the disclosure of which is incorporated by reference.

FIELD OF THE INVENTION

The invention relates to methods for determining a haplotype for an organism.

BACKGROUND

Examining a person's genes can reveal if that person has a genetic disease or even if he or she is a latent carrier of a disease, at risk of passing the disease on to his or her children. The information is the person's genes can be revealed by DNA sequencing. The DNA sequencing technologies known as next-generation sequencing (NGS) are capable of sequencing an entire human genome in under a day and for under $1,000. See Clark, Illumina announces landmark $1,000 human genome sequencing, Wired, 15 Jan. 2014.

However, the most informative view of a person's genes requires knowing his or her "haplotype". Humans have two copies of each of their chromosomes, one inherited from the father and the other from the mother. There is variation between the two chromosomes of a pair. Most of that variation appears in the form of single nucleotide polymorphism (SNPs). For any heterozygous SNP, a person has a different allele on each chromosome at the location of the SNP. Those alleles that appear on the same chromosome can be said to belong to the same haplotype. Unfortunately, standard methods such as sequencing collect only genotype information but do not assign the alleles to haplotypes. Existing attempts to do so require comparison to a reference haplotype (e.g., Yang, 2013, Leveraging reads that span multiple single nucleotide polymorphisms for haplotype inference from sequencing data, Bioinformatics 29(18): 2245-2252) or construction of a graph based on a SNP-fragment matrix that artificially reduces the two alleles of a SNP to a binary 0 or 1 score (e.g., Aguiar and Istrail, 2012, HapCompass: A fast cycle basis algorithm for accurate haplotype assembly of sequence data, J Comp Biol 19(6): 577-590). Reducing the alleles of a SNP to a binary code is unsatisfactory for at least two reasons. First, the resulting matrix and graph will require an extrinsic "key" to decode the entries back into the haplotype, which adds a separate lookup step that is very time consuming if a computer is going to generate reports of the haplotypes in any high-throughput environment. Second, even though a heterozygous SNP will typically only have two alleles in a diploid genome, those SNPs may have as many as four alleles within a population and each allele may have independent medical significance. If SNP alleles are encoded as a binary 1 or 0, there is no basis for comparison among data sets. For example, if Smith has two heterozygous SNPs for which the first haplotype is AC and the second haplotype is GC, and Jones—at the homologous locations—has the first haplotype GT and the second haplotype TT, once Smith's haplotypes are defined as 11 and 01, respectively, there is left no way to define Jones' haplotypes that provides for a meaningful comparison to Smith's.

SUMMARY

The invention provides a method for determining a haplotype by transforming alleles found in sequence fragments into vertices in a graph with edges connecting vertices for alleles that appear together in a sequence fragment. A community detection operation can be used to infer the haplotype from the graph. For example, the allele nodes may be assigned to blocks. Taking an assignment of the alleles to a block as representing a supposition of a haplotype, it is possible to calculate the probability of the graph given the supposition represented by that block. The assignment of alleles to a block that maximizes the probability of the graph—the maximum likelihood assignment—may be taken to represent the actual haplotype from the organism's genome. That maximum likelihood block of alleles is produced by the community detection operation and can be included in a report of the organism's haplotype. Methods of the invention may further include a graph parsing step wherein conflicting phases are identified and the edges representing the lesser-supported phase are trimmed from the graph prior to the community detection operation. Where the sequence fragments include sequence reads generated by sequencing a diploid or multiploid genome of an organism, the method can be used to produce a report that includes the haplotype of the SNPs found in the genome of that organism. Since the haplotype in the report is drawn from a graph in which the nodes represent the actual nucleotide of the allele of a SNP, no de-coding step referencing an extrinsic key is required to read from the graph and provide the haplotype. Since each node in the graph represents the nucleotide found at that SNP in that genome, corresponding portions of different graphs can be meaningfully compared to one another.

In certain aspects, the invention provides a method for determining a haplotype. The method includes obtaining a plurality of sequence fragments from a genome of an organism and transforming the sequence fragments into a graph comprising a vertex for each allele of a plurality of SNPs found in the plurality of sequence fragments and an edge for each pair of the alleles that are found in one of the fragments. For each pair of the plurality of SNPs for which alleles are found in one of the fragments, a most-supported phase for alleles of that pair of SNPs is determined and any edge from the graph representing a less-supported phase for the alleles of that pair of SNPs is removed. The method includes performing a community detection operation on the largest contiguous component of the graph remaining after the edge removal to assign each vertex of that component to a haplotype. Creating the graph is performed by a computer system comprising a processor coupled to a memory subsystem. Preferably, the graph uses pointers to identify a physical location in the memory subsystem where each vertex is stored. In some embodiments, creating the graph includes creating the vertices using index-free adjacency wherein each vertex includes a pointer for each connected vertex to which that vertex is connected by an edge. The pointer identifies a location of the connected vertex. Preferably, the pointer identifies a physical location in the memory subsystem where the connected vertex is stored. In certain embodiments, creating the graph includes creating vertex objects and edge objects that each include an adjacency list that stores a list of such objects that it is adjacent to. Each adjacency list includes pointers to specific physical locations within the memory subsystem for the adjacent objects.

The community detection operation may include finding an assignment of each allele vertex to one or more blocks wherein the probability of the graph given the assignment is optimized. The likelihood maximizing assignment of alleles to a block may include (i) initially arbitrarily assigning each node to one of the two blocks; (ii) calculating the probability of graph given the assignment; (iii) making a change to the assignment; (iv) repeating steps (ii) and (iii) to create a chain of assignments; and (v) selecting from the chain the assignment wherein the probability of the graph given that assignment is optimized. Steps (ii) and (iii) may be repeated while modifying the block membership of each vertex in a random fashion and accepting or rejecting the modification according to a change in the probability of the assignment associated with that modification.

In certain embodiments, the plurality of sequence fragments are obtained from a genome of an organism by sequencing nucleic acid from a sample from the organism. The organism may be a patient. The method may include producing a report showing the haplotype for the patient. The reported haplotype may cover all or substantially all (e.g., at least 85%) of a chromosome of the patient. A sequence fragment may be either a sequence read or a pair of paired-end sequence reads.

Aspects of the invention provide a method for determining a haplotype. The method includes obtaining a plurality of sequence fragments generated by sequencing nucleic acid from a genome of a patient; creating—using a computer system comprising a processor coupled to a memory subsystem—a graph comprising a vertex for each allele of each of a plurality of SNPs found in the plurality of sequence fragments and an edge for each subset of the alleles that are found in one of the fragments, wherein the graph uses pointers to identify a physical location in the memory subsystem where each vertex is stored; determining, for each pair of the plurality of SNPs for which alleles are found in one of the fragments, a best-supported phase for alleles of that pair of SNPs and removing at least one edge from the graph representing a less-supported phase for alleles of that pair of SNPs; using a community detection operation such as finding a maximum likelihood assignment of each vertex to one or more blocks wherein the probability of the graph given the assignment is maximized, thereby assigning each allele to a haplotype; and producing a report showing the haplotype for the patient. Finding the maximum likelihood assignment may include (i) initially arbitrarily assigning each vertex to one of the two blocks; (ii) calculating the probability of the graph given the assignment; (iii) making a change to the assignment; (iv) repeating steps (ii) and (iii) to create a chain of assignments; and (v) selecting from the chain the assignment wherein the probability of the graph given that assignment is optimized. Steps (ii) and (iii) may be repeated to define a Monte Carlo Markov chain (MCMC) by modifying the block membership of each vertex in a random fashion and accepting or rejecting the modification according to a change in the probability of the assignment associated with that modification. The method may include sequencing nucleic acid from a subject or patient and producing a report showing the haplotype of the subject or patient.

In some aspects, the invention provides a system for determining a haplotype. The system includes a processor coupled to a memory subsystem. The system is operable to obtain a plurality of sequence fragments generated by sequencing nucleic acid from a genome of a patient and create a graph comprising a vertex for each allele of each of a plurality of SNPs found in the plurality of sequence fragments and an edge for each pair of the alleles that are found in one of the fragments, wherein the graph uses pointers to identify a physical location in the memory subsystem where each vertex is stored. The system may determine, for each pair of the plurality of SNPs for which alleles are found in one of the fragments, a best-supported phase for alleles of that pair of SNPs and remove at least one edge from the graph representing a less-supported phase for alleles of that pair of SNPs. The system is operable to find a maximum likelihood assignment of allele vertices to one or more blocks that maximizes the probability of the graph, thereby assigning each allele to a haplotype. The system produces a report showing the haplotype for the patient.

The system may find the maximum likelihood block by (i) initially arbitrarily assigning vertices to one or more blocks; (ii) calculating the probability of the graph given the assignment; (iii) making a change to the assignment; (iv) repeating steps (ii) and (iii) to create a chain of assignments; and (v) selecting from the chain the assignment wherein the probability of the graph given that assignment is optimized. In certain embodiments, the system repeats steps (ii) and (iii) to define a MCMC by modifying the block membership of each vertex in a random fashion and accepting or rejecting the modification according to a change in the probability of the assignment associated with that modification.

The system preferably creates the graph using pointers to identify a physical location in the memory subsystem where each vertex is stored. In some embodiments, creating the graph includes creating the vertices to use index-free adjacency wherein each vertex includes a pointer for each connected vertex to which that vertex is connected by an edge. The pointer identifies a location of the connected vertex. Preferably, the pointer identifies a physical location in the memory subsystem where the connected vertex is stored. In certain embodiments, creating the graph includes creating vertex objects and edge objects each includes an adjacency list that stores a list of such objects that it is adjacent to. Each adjacency list includes pointers to specific physical locations within the memory subsystem for the adjacent objects.

DETAILED DESCRIPTION

The invention provides a method for determining a haplotype for an organism by transforming alleles for SNPs found in sequence fragments into vertices in a graph. The invention uses alleles as vertices, resulting in graphs from which identifiable communities of related alleles are found to emerge. This allows for the application of community detection operations (operations such as those that may be used to identify communities in social networks) to haplotype alleles post-graph construction. A sequence fragment that includes multiple alleles is transformed into an increment to an edge weight for an edge that connects those alleles. This produces a graph in which alleles of SNPs are represented by vertices and those vertices are connected by weighted edges. Each edge represents a potential phasing of the connected alleles and the weight of that edge represents the amount of support for that phasing that can be found in the sequence fragments. Thus the sequence fragments, which may be obtained in a fragmented linear structure such as one or more FASTQ files, are transformed into a graph and the graph exhibits a topology that represents potential relationships among the alleles as found in the organism.

To report the haplotype phasing of the alleles in the organism, the graph can be trimmed. Specifically, where a pair of heterozygous SNPs yields a pair of edges that represent incompatible phases in the graph, the weight of those edges can be compared to see which edge has lesser support from the sequence fragments. The edge with less support can be removed. A community detection operation can be performed on the resulting graph to report a haplotype of the organism. The community detection operation may include assigning alleles from the graph to a block and determining a probability of the graph is given the assignment of those alleles to that block. Different assignments can be made to test a series of different blocks. The block (i.e., the assignment) that gives the highest probability for the graph (the maximum likelihood block) can be reported as the haplotype of the organism. Methods of the invention may be used to determine a haplotype for any suitable set of sequence fragments such as sequence reads or pairs of paired-end reads. The read may represent any suitable genetic information of interest, such as a whole genome sequence of an organism or a transcriptome as analyzed by RNA-Seq. Methods of the invention may be used to phase alleles from any multiploid or diploid genome. In an exemplary embodiment, methods of the invention have been applied in the context of haplotyping in the BRCA genes.

Figure 1:
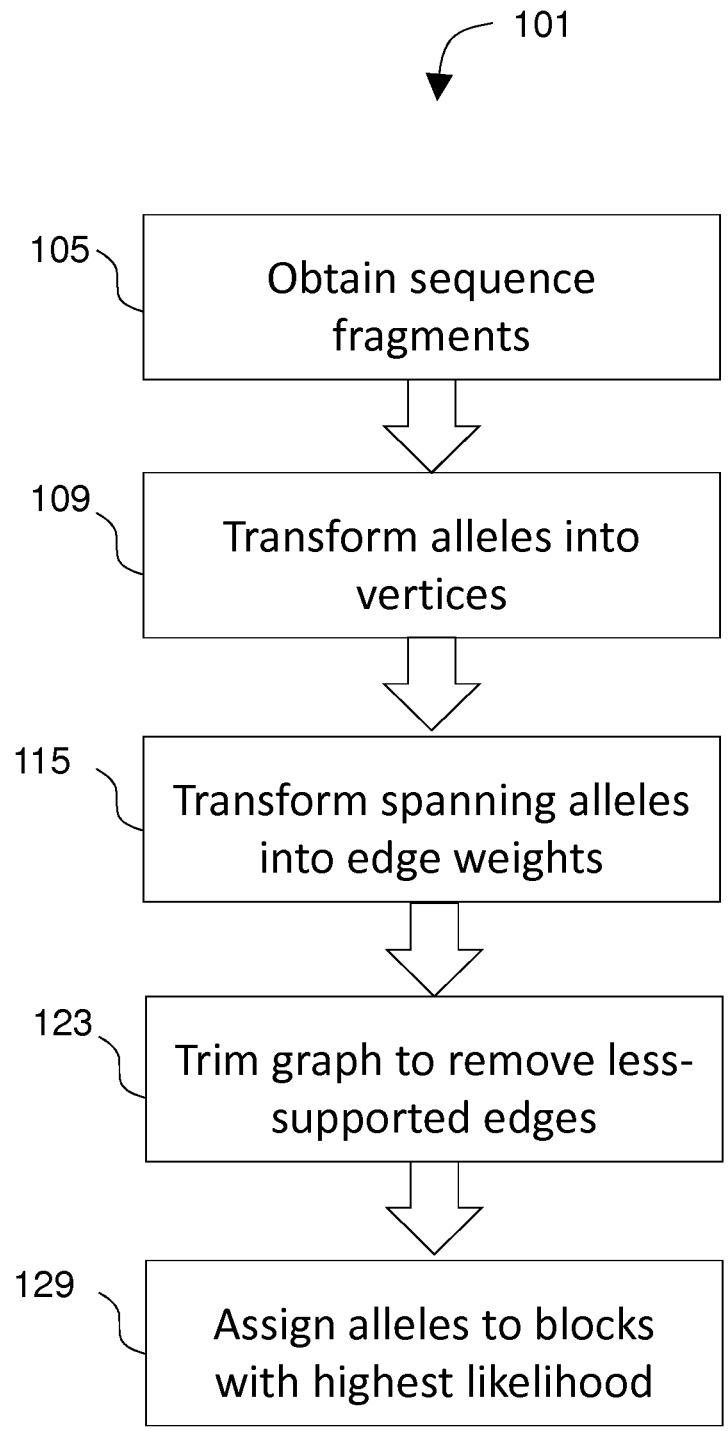
FIG. 1 diagrams a method for determining a haplotype.

FIG. 1 diagrams a method 101 for determining a haplotype. The method includes obtaining 105 a plurality of sequence fragments from a genome of an organism. A sequence fragment is generally a set of nucleotide sequence information reasonably assumed to be obtained from one chromosome. For example, a sequence fragment may be a sequence read or a pair of paired-end reads. Sequence reads may be generated by sequencing a sample that includes nucleic acid from the organism. Sequencing generates a plurality of reads. Reads according to the invention generally include sequences of nucleotide data anywhere from tens to thousands of bases in length. In some embodiments, PCR product is pooled and sequenced (e.g., on an Illumina HiSeq 2000). Raw .bcl files are converted to qseq files using bclConverter (Illumina). FASTQ files are generated by "debarcoding" genomic reads using the associated barcode reads; reads for which barcodes yield no exact match to an expected barcode, or contain one or more low-quality base calls, may be discarded. Reads may be stored in any suitable format such as, for example, FASTA or FASTQ format. FASTA is originally a computer program for searching sequence databases and the name FASTA has come to also refer to a standard file format. See Pearson & Lipman, 1988, Improved tools for biological sequence comparison, PNAS 85:2444-2448. A sequence in FASTA format begins with a single-line description, followed by lines of sequence data. The description line is distinguished from the sequence data by a greater-than (">") symbol in the first column. FASTQ files are similar to FASTA but further include a line of quality scores. Typically, sequence reads will be obtained 105 in a fragmented, linear format such as a FASTQ file.

The sequence fragments are analyzed to identify alleles at a plurality of SNPs in the organism's genome. Any suitable variant-calling operation can be performed. For example, the sequence reads can be aligned to a reference to identify SNPs, and the allele for the SNP in the organism can be determined from the alignment. A variety of variant calling operations are known in the art. For example, where the organism is a person, variant calling can include aligning sequence reads to a reference such as the human genome (e.g., the hg18 reference genome) and reporting SNP alleles in a format such as a Sequence Alignment Map (SAM) or a Variant Call Format (VCF) file. In certain embodiments, reads are aligned to hg18 using Burrows-Wheeler Aligner version 0.5.7 for short alignments, and genotype calls are made using Genome Analysis Toolkit. See Li & Durbin, 2009, Fast and accurate short read alignment with Burrows-Wheeler Transform. Bioinformatics 25:1754-60 and McKenna et al., 2010, The Genome Analysis Toolkit: a MapReduce framework for analyzing next-generation DNA sequencing data, Genome Res 20(9):1297-1303, the contents of each of which are incorporated by reference. Alignment to hg18 and variant calling produces results ("variant calls") that may be stored as a sequence alignment map (SAM) or binary alignment map (BAM) file—comprising an alignment string (the SAM format is described, e.g., in Li, et al., The Sequence Alignment/Map format and SAMtools, Bioinformatics, 2009, 25(16):2078-9). Alignment strings known in the art include Simple UnGapped Alignment Report (SUGAR), Verbose Useful Labeled Gapped Alignment Report (VULGAR), and Compact Idiosyncratic Gapped Alignment Report (CIGAR) (Ning, Z., et al., Genome Research 11(10):1725-9 (2001)). These strings are implemented, for example, in the Exonerate sequence alignment software from the European Bioinformatics Institute (Hinxton, UK). CIGAR displays or includes gapped alignments one-per-line. CIGAR is a compressed pairwise alignment format reported as a CIGAR string. A CIGAR string is useful for representing long (e.g. genomic) pairwise alignments. A CIGAR string is used in SAM format to represent alignments of reads to a reference genome sequence. In a CIGAR string, each character is preceded by a number, giving the base counts of the event. Characters used can include M, I, D, N, and S (M=match; I=insertion; D=deletion; N=gap; S=substitution). The CIGAR string defines the sequence of matches/mismatches and deletions (or gaps). Additionally or alternatively, output from the variant calling may be provided in a variant call format (VCF) file. A typical VCF file 183 will include a header section and a data section. The header contains an arbitrary number of meta-information lines, each starting with characters '##', and a TAB delimited field definition line starting with a single '#' character. The field definition line names eight mandatory columns and the body section contains lines of data populating the columns defined by the field definition line. The VCF format is described in Danecek et al., 2011, The variant call format and VCFtools, Bioinformatics 27(15):2156-2158. Further discussion of methods for variant calling may be found in U.S. Pub. 2013/0073214; U.S. Pub. 2013/0345066; U.S. Pub. 2013/0311106; U.S. Pub. 2013/

0059740; and U.S. Pub. 2012/0157322, the contents of each of which are incorporated by reference.

Variant calling gives an allele for each SNP. By comparing the sequence fragments to a reference to call variants, the alleles of heterozygous SNPs are identified. However, existing variant calling methods give genotype information but do not give a haplotype.

Figure 2:
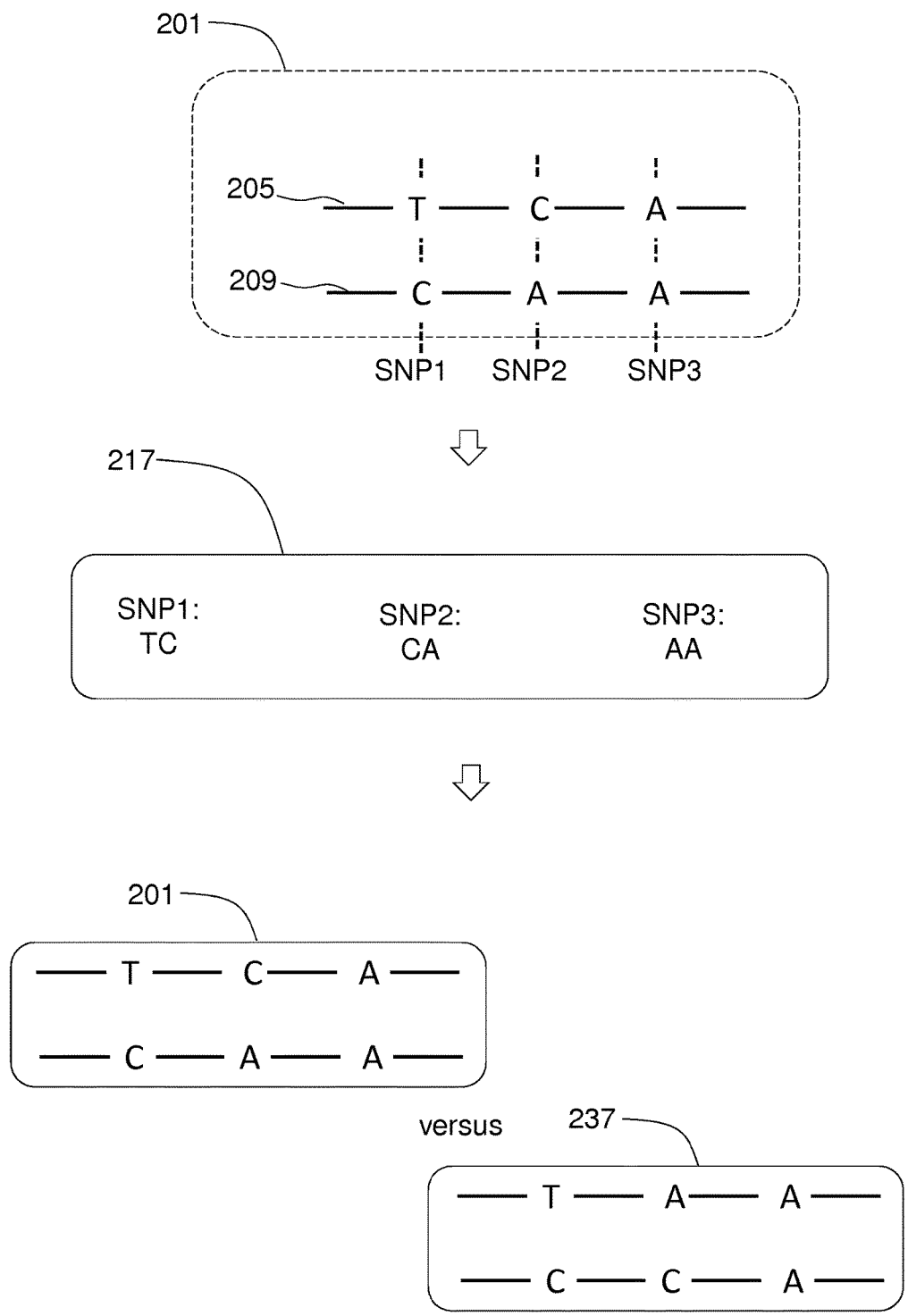
FIG. 2 illustrates the haplotyping problem that is addressed.

FIG. 2 illustrates the haplotyping problem that is addressed. A maternal chromosome 205 and a paternal chromosome 209 are subject to sequencing to produce a plurality of fragments. A genome 201 includes a plurality of SNPs. The maternal chromosome 205 has alleles T, C, and A for SNP1, SNP2, and SNP3, respectively. The paternal chromosome 209 has alleles C, A, and A for SNP1, SNP2, and SNP3, respectively. Variant calling produces the genotype 217, which includes heterozygous SNP1 and SNP2. The variant calling does not give information to arrive at the correctly phased genotype 201 or the incorrectly phased genotype 237. Thus variant calling is not capable of determining a haplotype from sequence fragments. In contrast, the method 101 produces a haplotype from sequence fragments.

Figure 3:
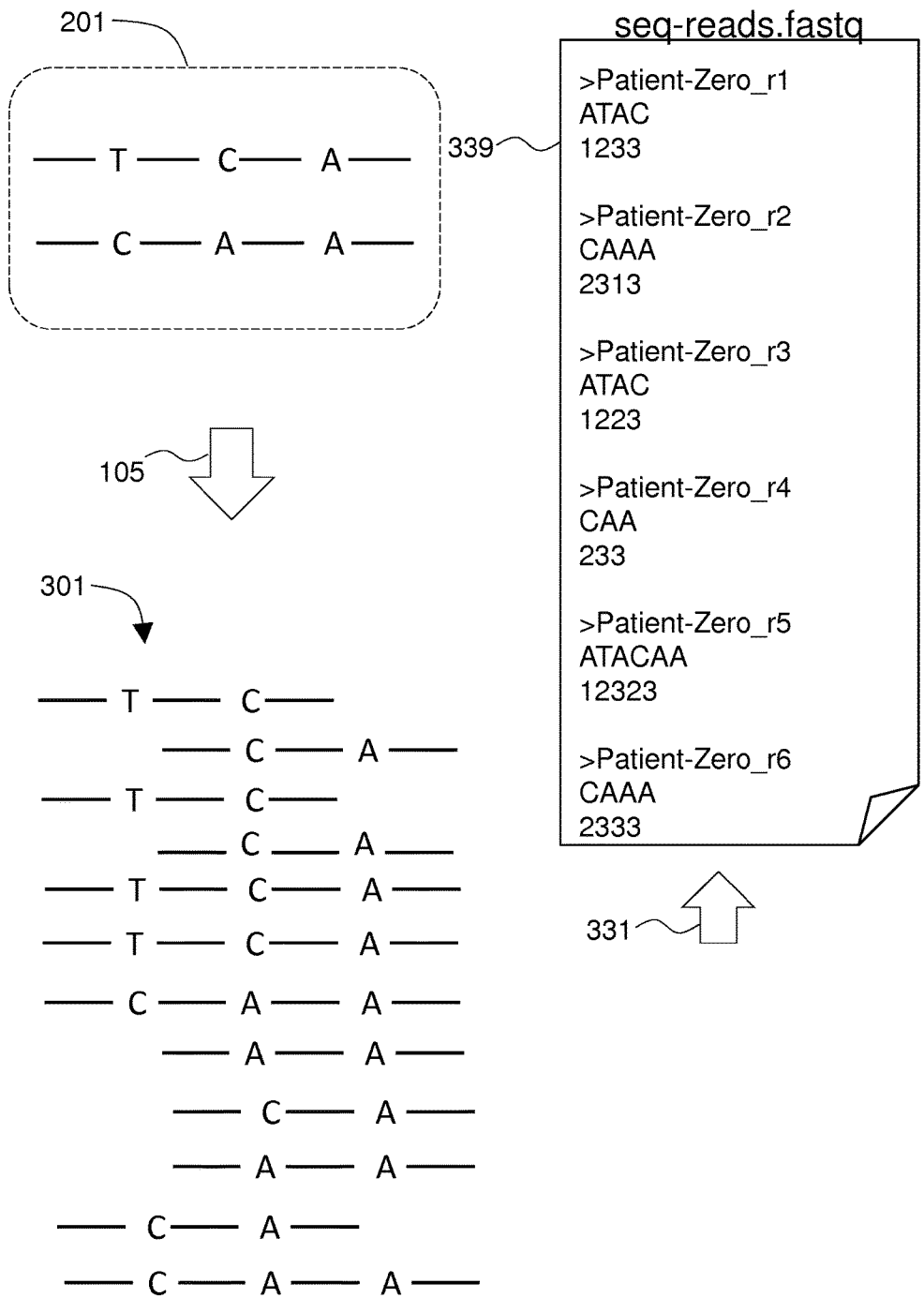
FIG. 3 shows obtaining a set of sequence fragments.

FIG. 3 shows obtaining 105 a set of sequence fragments 301. To aid in illustration, the sequence fragments are shown in the cartoon of FIG. 3 in an aligned form, but they will typicall not be aligned until an alignment operation is performed (the depiction in FIG. 3 is to facilitate understanding). The genome 201 may be sequenced to produce reads shown in FIG. 3 as a cartoon of a set 301 of reads. The reads may be represented 331 by an electronic file 339, such as a FASTQ file. The electronic file 339 is a format that can be accessed by a computer system to transform alleles into nodes.

All read fragments covering heterozygous SNPs can be collected (taking the set of heterozygous SNPs identified by your favorite variant-calling algorithm). A fragment consists of a read and any other reads associated with it, for instance both reads in a paired-end read pair. Those will be used to create a graph comprising a vertex for each allele of each of a plurality of SNPs found in the plurality of sequence fragments and an edge for each subset of the alleles that are found in one of the fragments. Building an initial graph can include using alleles as vertices and setting the weight of each vertex to the number of reads supporting the allele (i.e., the number of reads in which the allele appears).

Figure 4:
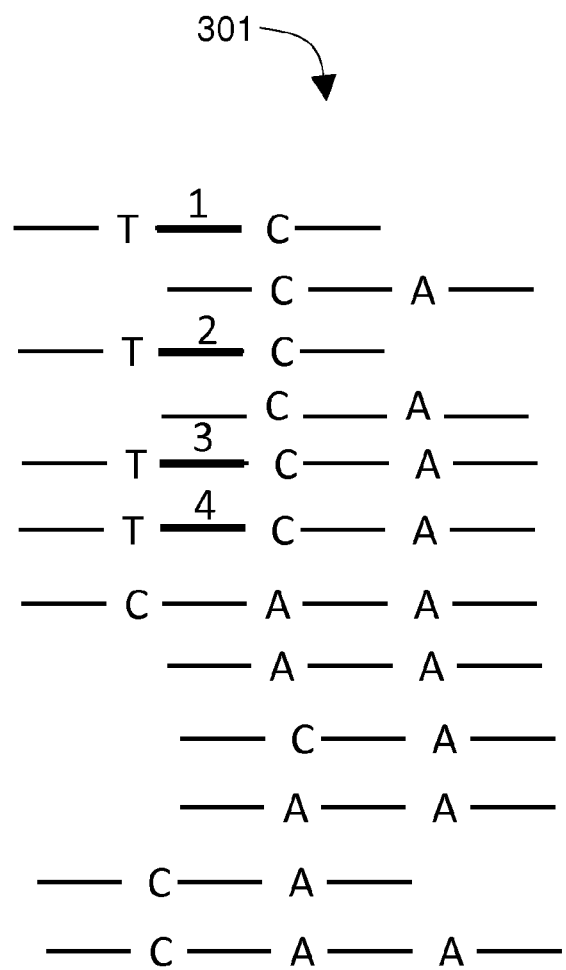
FIG. 4 illustrates transforming alleles into vertices to create a graph.
Figure 4:
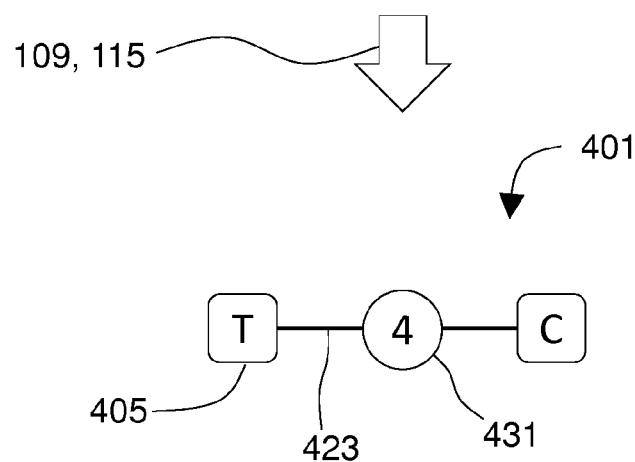

FIG. 4 illustrates an intermediate stage in transforming 109 those alleles into vertices to create a graph 401 that includes a vertex 405 for each allele of each of a plurality of SNPs found in the sequence fragments. A computer system that includes a processor coupled to a memory subsystem is used to transform 109 each allele into a vertex 405. The computer system is used to create 115 an edge 423 between pairs of nodes 405 for all alleles found in a given fragment, setting the edge weight 431 to the number of times that edge has been observed in fragments. Any sequence fragment that spans two or more SNPs and includes alleles for those SNPs shows the phasing of those SNPs in the genome of the organism. Method 101 includes transforming 115 those fragments that span multiple SNPs into edge weights 431. For any pair of alleles that are found together on a fragment, an edge 423 is created in the graph connecting the two vertices that represent those alleles. That edge 423 is given a weight 431 indicating a number of the fragments that includes that pair of alleles.

In certain embodiments, the graph 401 is implemented using index free adjacency. Creating the graph 401 may include creating the vertices 405 to use index-free adjacency wherein each vertex 405 includes one pointer for each connected vertex 405 to which that vertex is connected by an edge 423. Each pointer identifies a location of the connected vertex. Identifying the location of a connected vertex by a pointer includes identifying a physical location in the memory subsystem where the connected vertex is stored.

In some embodiments, the graph 401 is implemented using adjacency lists. Creating the graph 401 comprises creating vertex objects 405 and edge objects 423 that each includes an adjacency list that stores a list of such objects that it is adjacent to. Each adjacency list comprises pointers to specific physical locations within the memory subsystem for the adjacent objects.

Figure 5:
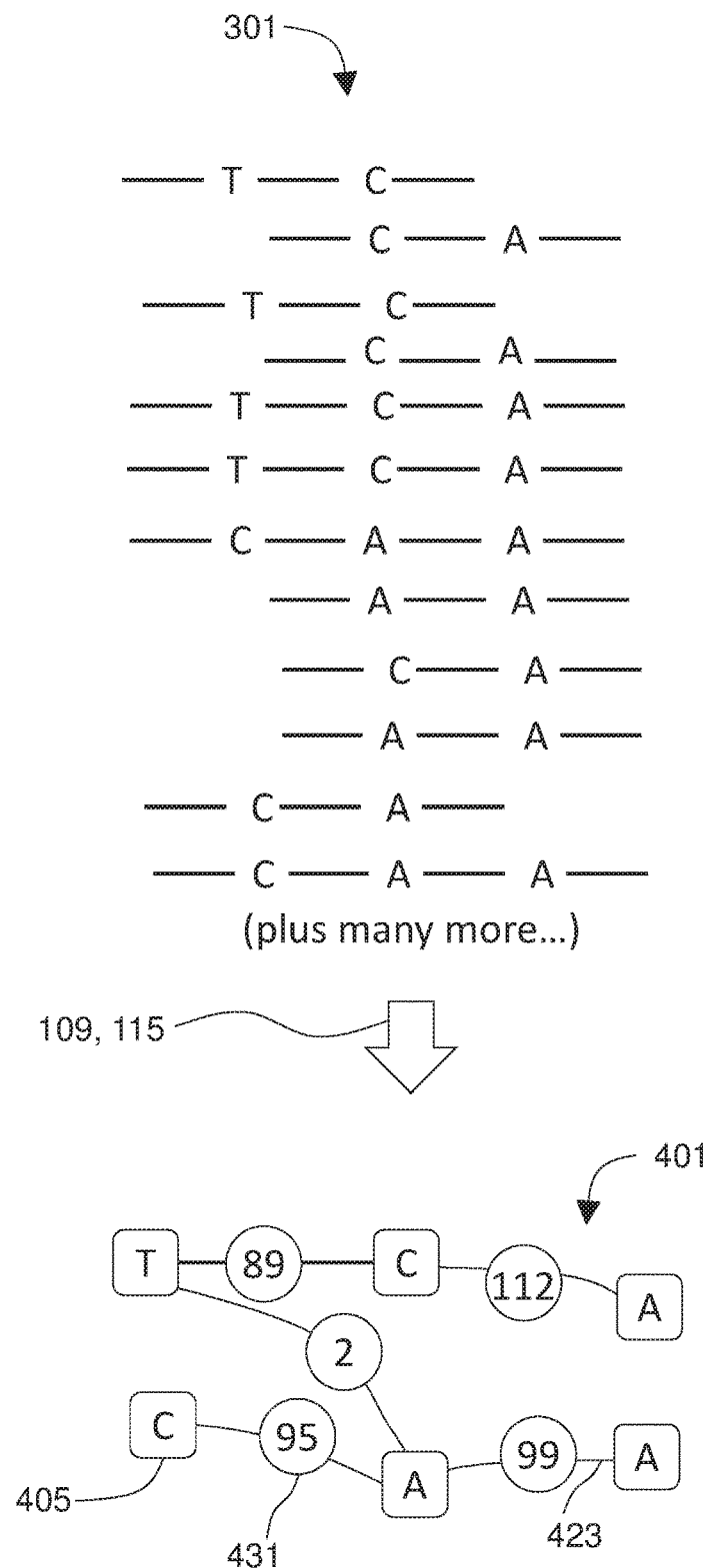
FIG. 5 illustrates the transformation of a set of sequence fragments into a graph.

FIG. 5 illustrates the transformation of a set of sequence fragments 301 into a graph 401 for genome 201 according to the described method. The system can keep track of the loci at which the SNPs occur (e.g., by alignment/comparison to a reference/variant calling) thus tracking which of the the —C-A-fragments are subsets of the -T—C—A-chromosome or the —C-A-A-one. Thus it can be seen that graph 401 represents alleles at locations. Note that since alleles are used for vertices, each edge 423 and its weight 431 represent one relationship—the relationship between the two alleles. In existing approaches that use loci as vertices, the edge weight effectively represents 4 or more relationships, between all the alleles present at each locus. Collapsing this information into one dimension in those approaches, the edge weight, necessarily results in loss of information, and through the sign of the edge weight also essentially predetermines the phasing of the alleles. In contrast, in the method 101 of the invention, alleles become vertices and each potential phase relationship may have its own edge. (Of course, in certain embodiments, one could instead associate alleles with edges and relationships as vertices.) The cartoon graph 401 in FIG. 5 includes six nodes 405 and five edges 423. A graph created for a gene or genome on real-world data will typically be much larger than this.

Figure 6:
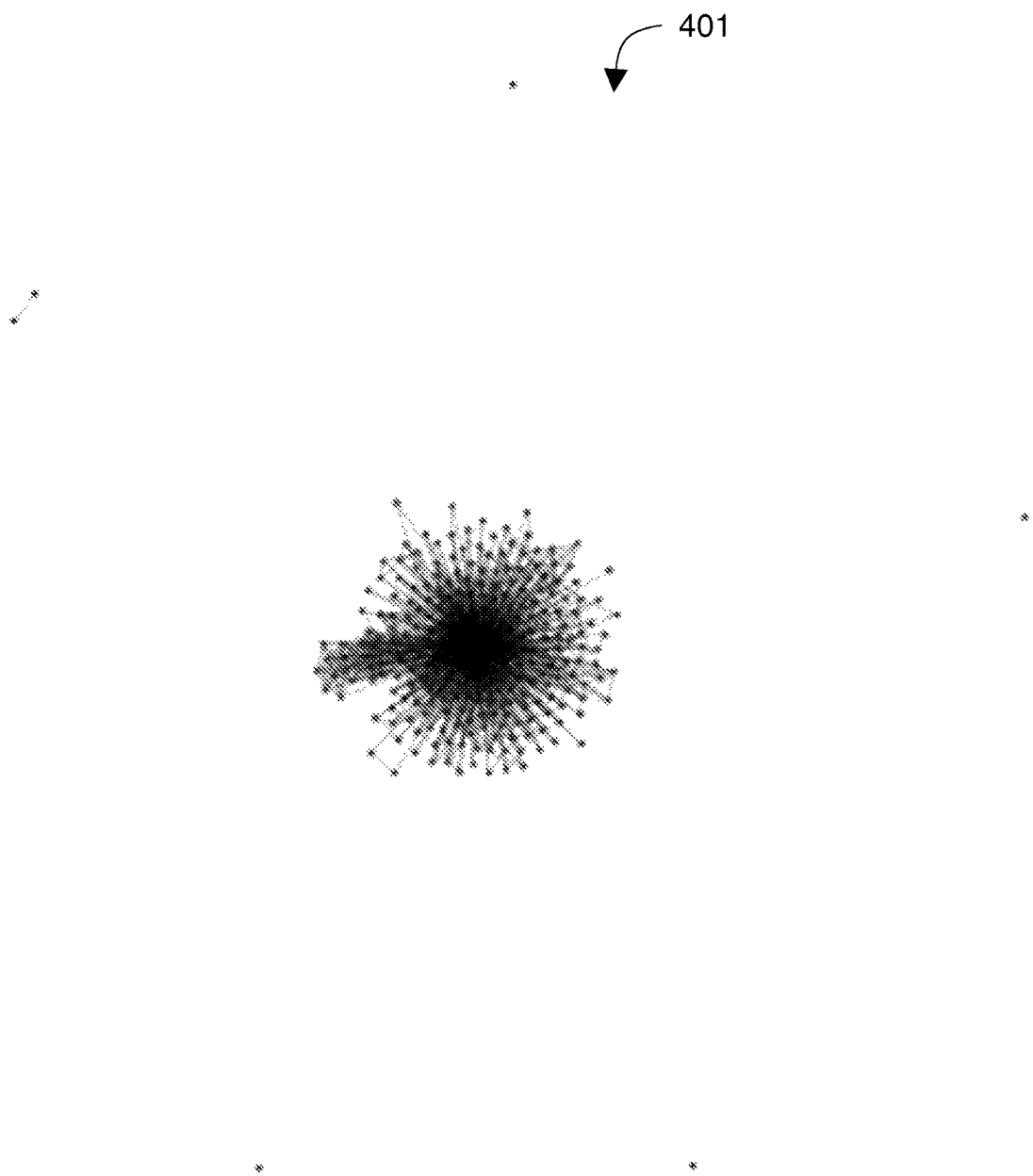
FIG. 6 shows a graph from a sample from the BRCA1 HAP1 region.

FIG. 6 shows what results in creating such a graph from a sample from the BRCA1 HAP1 region. This initial graph represents all of the data, unlike the initial graphs created using existing methods. However it is relatively tangled and still not well-suited to community detection. Graph 401 as shown in FIG. 6 contains many nodes and edges. However, in the method 101 of the invention, since each potential phase relationship may have its own edge 423, there is an opportunity to remove edges 423 that are not well supported by the input article 339—the set of sequence fragments 301.

The method 101 can remove edges by trimming 123 the graph to remove lesser-supported edges. For each pair of the plurality of SNPs for which alleles are found in one of the fragments, a most-supported phase for alleles of that pair of SNPs is determined. Any edge representing a less-supported phase for the alleles of that pair of SNPs is removed. The computer system can perform an operation to identify edges that are inconsistent with one another, in that they result in a chain that contains conflicting alleles. The following steps describe how the system can pare down some of these inconsistent edges. For each pair of the plurality of SNPs for which alleles are found in one of the fragments, determine a most-supported phase for alleles of that pair of SNPs and remove any edge from the graph representing a less-supported phase for the alleles of that pair of SNPs. In a preferred embodiment, each edge weight is normalized by dividing it by the smaller of the weights of its two vertices, as shown in Equation 1.

$$\text{edge\_w} = \frac{\text{edge\_w}}{\min(\text{src\_w}, \text{tgt\_w})} \quad (1)$$

Normalization corrects for variability and inconsistency in coverage by looking not at the absolute number of times an allele-pair occurs, but rather the number of times it occurs relative to the number of occurrences of the least-common of the alleles in the pair (i.e., relative to the number of times it "has a chance" to occur).

Thus the system can address two pairs of conflicting alleles, i.e., two pairs of alleles which cannot co-occur because they are alternatives to one another. For example, A and A' may be two alleles of SNP X and B and B' may be two alleles of SNP Y. One non-conflicting pair of combinations of the two is labeled as "in-phase", and the other "cross-phase". In this example, the A-B and A'-B' combinations are "in phase", and the A'-B and A-B' combinations are "cross-phase". Note that the "in phase" combinations are inconsistent with the "cross-phase" combinations (and vice versa) because of the transitive property—e.g., if A and B' co-occurred and A and B also co-occurred, then B and B' would also be co-occurring, creating a conflict.

For each such pair of SNPs, trimming 123 can proceed by adding up the weights of the edges supporting "in-phase" combinations and the weights of the edges supporting "cross-phase" combinations, and calculating a phase ratio according to Equation 2.

$$\text{phase\_ratio} = \frac{\text{sum(in\_phase\_w)} - \text{sum(cross\_phase\_w)}}{\text{sum(in\_phase\_w)} + \text{sum(cross\_phase\_w)}} \quad (2)$$

The numerator results in a positive number if there is more support for the "in-phase" combinations, and a negative number if there is more support for "cross-phase"; the denominator normalizes the resulting ratio. Note that the normalization step (dividing by the sum of sums) is optional at this stage. The normalization step is potentially useful to provide some indication of the strength/confidence of the phase determination (e.g., whether the evidence strongly favors either cross- or in-phase, or is instead relatively evenly balanced/indeterminate). Using such a determination, the system is operable to remove all "cross-phase" edges when the phase ratio is >0, and remove all in-phase edges when the phase ratio <0. Thus, any edge from the graph 401 representing a less-supported phase for the alleles of that pair of SNPs is removed and the graph is trimmed 123.

Figure 7:
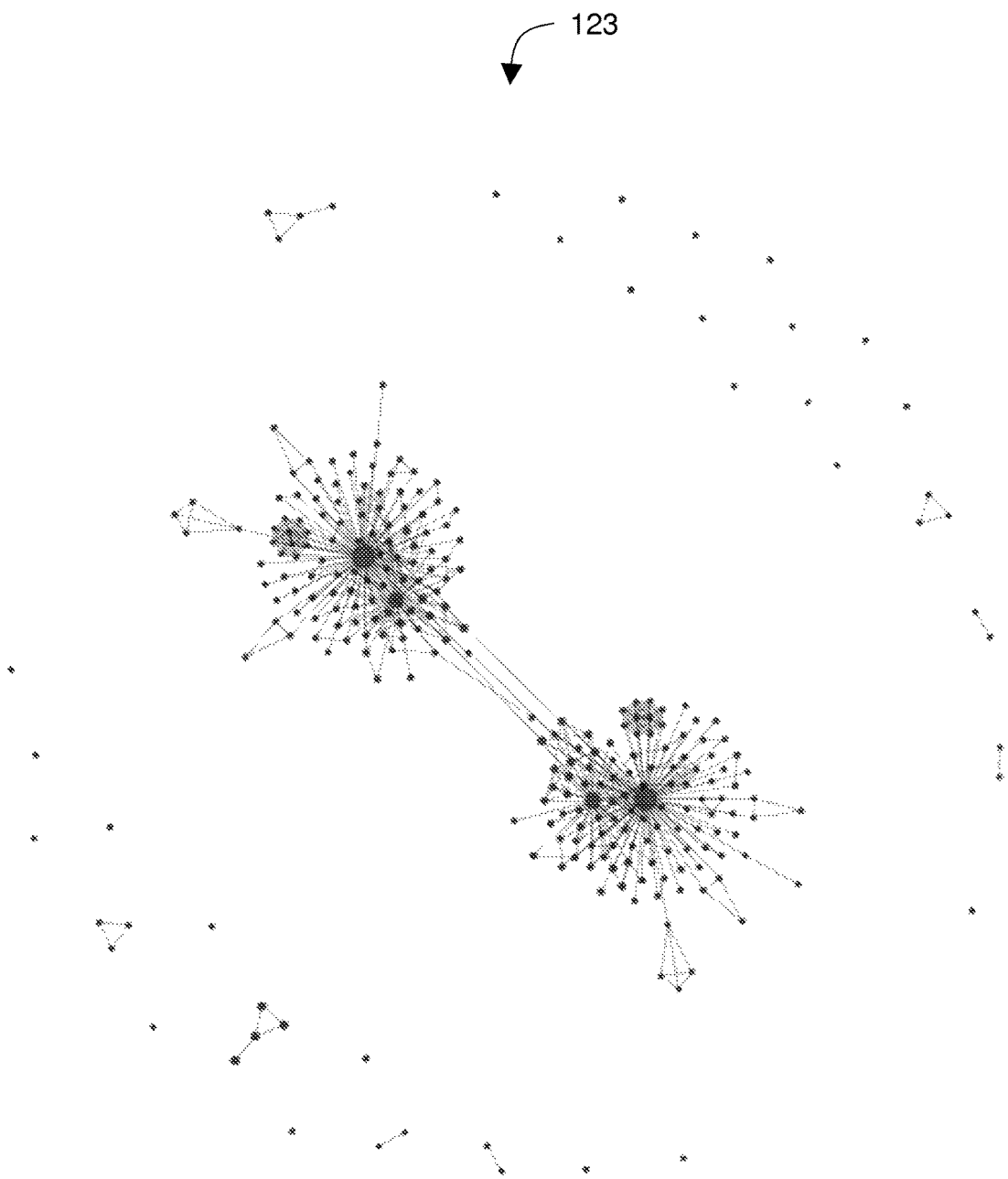
FIG. 7 shows the graph that results from the trimming.

FIG. 7 shows the graph 401 that results from the trimming 123. The resulting graph shown in FIG. 7 is much cleaner than the version shown in FIG. 6 and results in two obvious clusters of alleles. The computer system is operable to address either the biggest component, or two biggest components (in case of full separation of haplotypes, i.e., no connection between the two large clusters). In certain embodiments, two biggest components are addressed only when size of the two is similar, where similarity is determined by difference in number of vertices in relation to an arbitrary cutoff (expressed either in terms of number of vertices or percentage of total vertices). The computer system performs a community detection operation on the one or two largest contiguous components of the graph remaining after the edge removal to assign each vertex of that component to a haplotype.

Any suitable community detection operation can be performed. Community detection is an analytical technique useful in graph data analytics. Methods of community detection provide for finding groups of densely connected nodes with few connections to nodes outside of the group. For haplotyping, disjoint community detection (as compared to overlapping community detection) will typically be employed. Disjoint communities are ones in which each node belongs to at most one community. Disjoint community detection includes graph partitioning to divide a graph into two partitions. Various suitable approaches may be employed. For example, "Walktrap" refers to a method that uses random walks based on the assumption that a random walk will likely get trapped in a community. See, generally, Harenberg, 2014, Community detection in large-scale networks: a survey and empirical evaluation, WIREs Comp Stat 6:426-439. Other suitable approaches include multithreaded community detection, starting with each node as a separate community and merging communities until a modularity function is maximized. In some embodiments, the community detection operation includes assigning alleles from the graph to a block and determining how likely the topology of the graph is given the assignment of those alleles to that block. One suitable implementation of a community detection operation includes a block partitioning method described in Peixoto, 2014, Efficient Monte Carlo and greedy heuristic for the inference of stochastic block models, Phys. Rev. E 89, 012804.

Figure 8:
FIG. 8 sketches certain steps in a block partitioning community detection operation.
Figure 8:
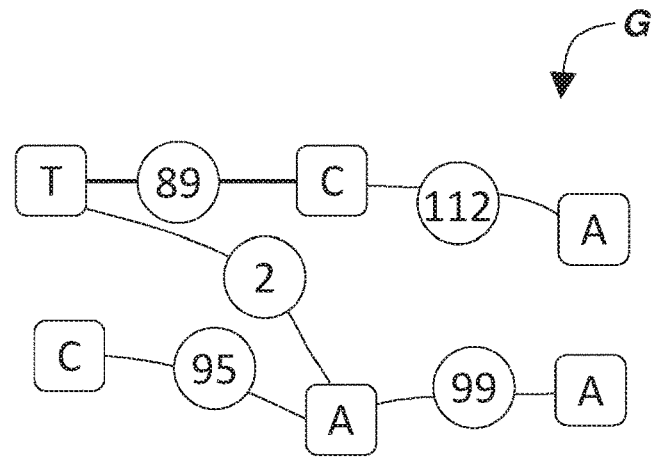
Figure 8:
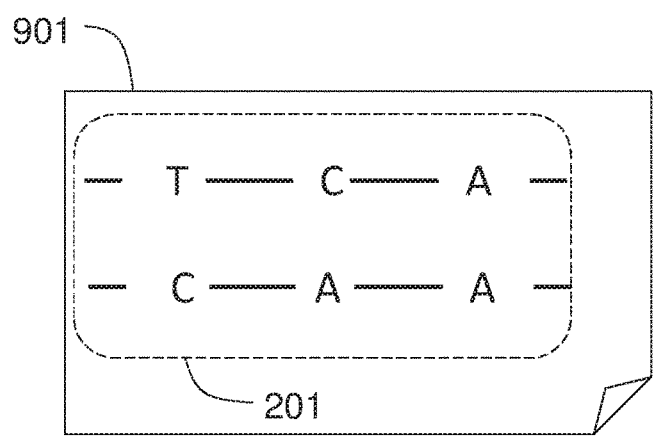

FIG. 8 sketches certain steps in a block partitioning community detection operation according to some embodiments. A graph G is presented and can be seen to include 6 vertices and 5 edges with edge weights ranging from 2 to 112. In one approach, an arbitrary set of the alleles represented in the graph G is assigned to a block B. If it is assumed that the data represents alleles from a diploid genome, since the system is performing a haplotyping operation, it may be suitable to assign half of the alleles to a block. In one embodiment, a system randomly selects three alleles and assigns those alleles to a block B1, so that B1 includes the alleles T, C, and A. The system can then calculate the probability that the graph G would have the topology and values that it does given the block B1. Any suitable community detection operation or method can be used to calculate the probability of the graph G. See, for example, Airoldi et al, 2007, Mixed membership stochastic blockmodels, JMLR or Yang, 2014, Community detection in networks with node attributes, proc IEEE ICDM '13, the contents of both of which are incorporated by reference for all purposes.

In one method to calculate the probability of the graph G given the assignments to blocks, label the two blocks group 1 and group 2 and denote by g, the group to which vertex I belongs. The edges in the network may be represented by an adjacency matrix having elements $A_{ij}=\{1$ if edge, 0 otherwise$\}$. The likelihood of generating a particular network or graph G, given the complete set of group memberships, which can be denoted by shorthand g, and the Poisson parameters denoted w, is:

$$P(G|g,w) = \prod_{i<j} \frac{\omega_{ij}^{A_{ij}}}{A_{ij}!} e^{-\omega_{ij}}, \quad (3)$$

where $\omega_{ij}$ denotes the expected number of edges between vertices i and j—either $\omega_{in}$ or $\omega_{out}$, depending on whether the vertices are in the same or different groups. Given the likelihood, one can maximize to find the most likely values of the groups, e.g., by iteratively varying the block assignments and selected the assignment giving the highest P. For additional detail see Newman, 2013, Community detection and graph portioning, arXiv:1305.4974v1, the contents of which are incorporated by reference for all purposes.

The system can then make a new assignment of alleles to a block B2. The system can then calculate the probability of graph G given the block B2. One suitable approach to arriving at block B2 is for the system to make a change to block B1. In some embodiments, the system makes a provisional change and tests the provisional change against some measure such as graph modularity and then accepts the provisional change only if the measure is satisfied according to a certain criteria. Additionally, the system can make a series of changes, which results in proceeding down a chain of blocks B1, B2, . . . , BN, and testing the probability of the graph G for each block. After a number of blocks have been tested, the system may select the block B that gave the maximum likelihood of all of the tested blocks. The system may then produce a report 901 in which the alleles from the maximum likelihood block are given as the haplotype for the organism's genome 201.

Figure 9:
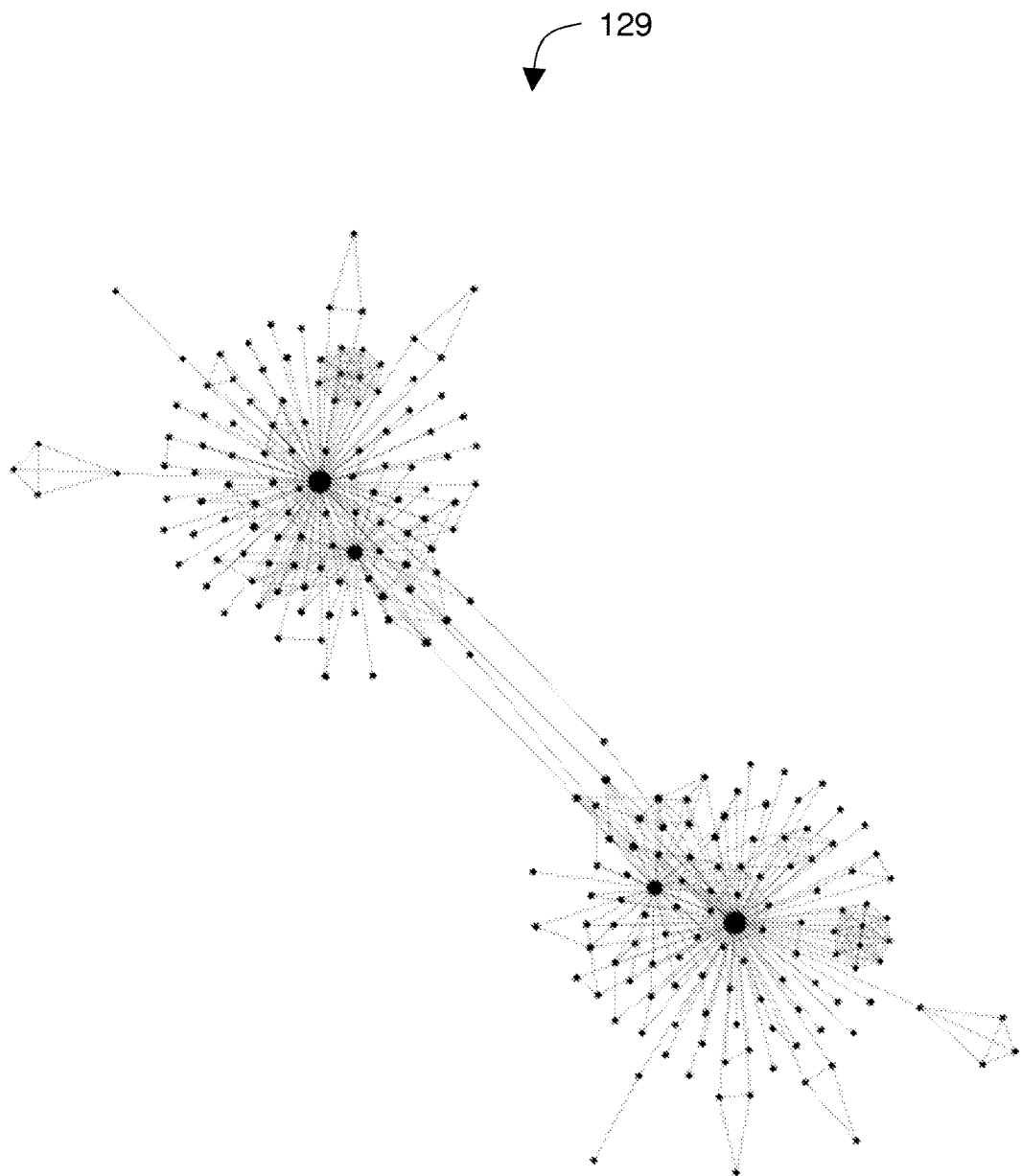
FIG. 9 shows a graph produced in an exemplary BRCA1 HAP1 proof-of-concept run.

FIG. 9 shows a graph 401 produced in an exemplary BRCA1 HAP1 proof-of-concept run. Application of the community detection operating includes assigning 129 alleles to the block that yielded the highest probability for graph 401. That operation resulted in 132 out of 139 SNPs successfully phased.

Figure 10:
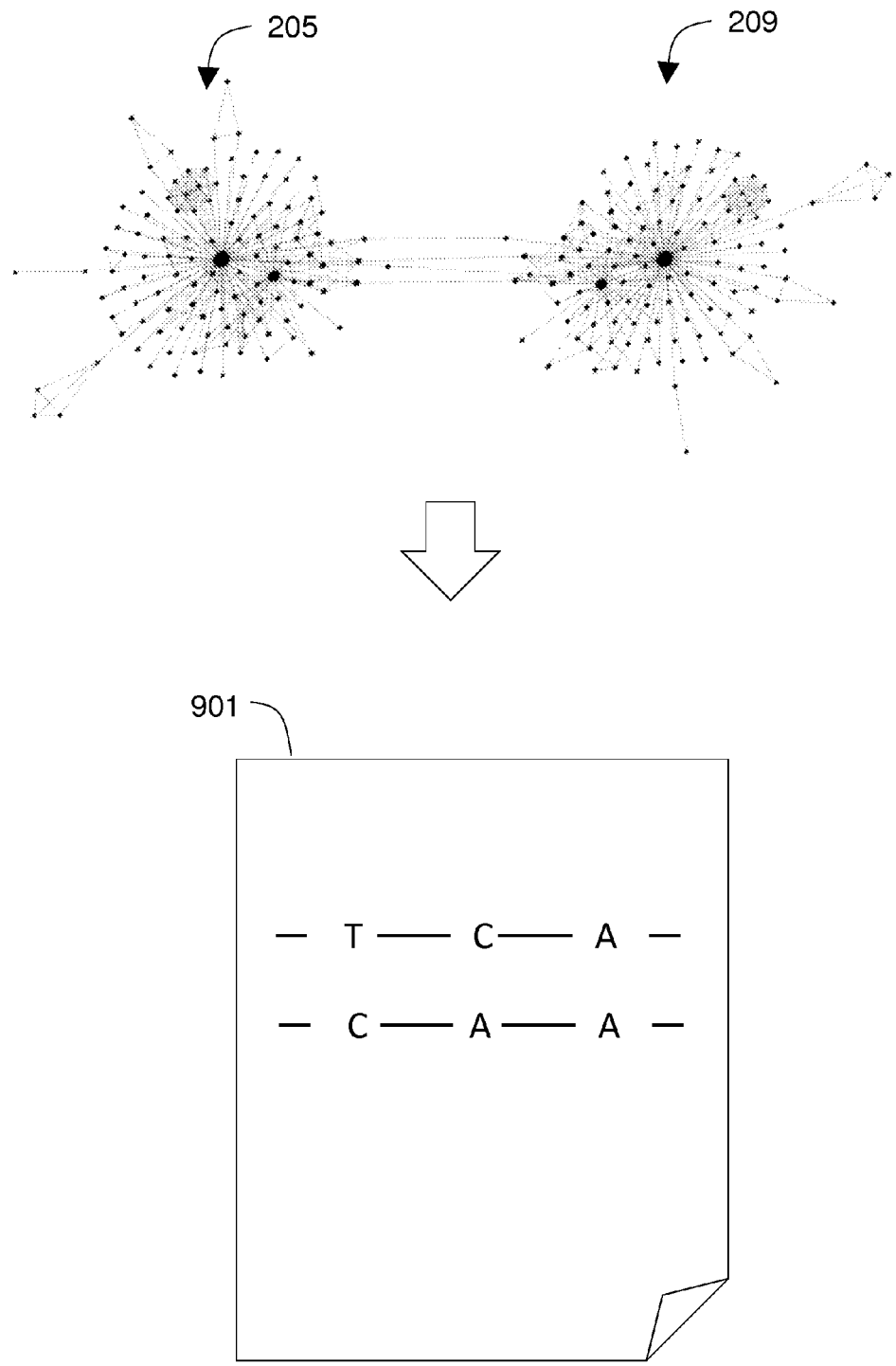
FIG. 10 illustrates producing a haplotype report.

FIG. 10 illustrates producing a report 901. In certain embodiments, the organism addressed by method 101 is a patient and the plurality of sequence fragments 301 are obtained by sequencing nucleic acid from the patient. The method 101 may include producing a report 901 showing the haplotype for the patient. Preferably the haplotype covers at least 85% of a chromosome of the patient. The report 901 is preferably produced by an input/output device of the computer system that performs the steps of method 101.

Figure 11:
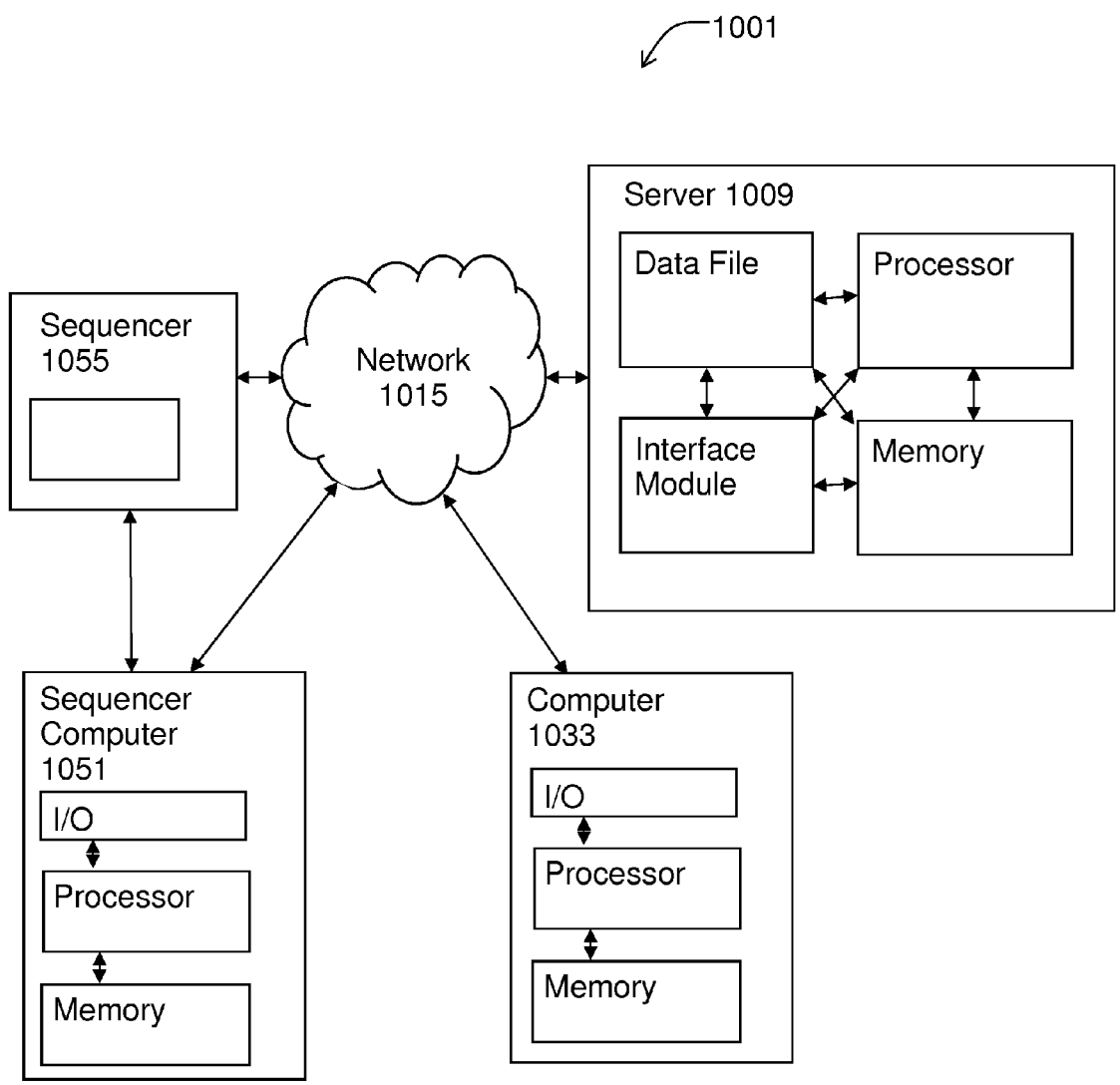
FIG. 11 is a diagram of a system for determining a haplotype.

FIG. 11 is a diagram of a system 1001 for determining a haplotype. The system 1001 includes at least one computer 1033. Optionally, the system 1001 may further include one or more of a server computer 1009 and a sequencer 1055, which may be coupled to a sequencer computer 1051. Each computer in the system 1001 includes a processor coupled to a memory device and at least one input/output device. Thus the system 1001 includes at least one processor coupled to a memory subsystem (e.g., a memory device or collection of memory devices). Using those mechanical components, the system 1001 is operable to obtain 105 a plurality of sequence fragments generated by sequencing nucleic acid from a genome of a patient. The system uses the processor to create a graph by transforming 109 each allele of each of a plurality of SNPs found in the plurality of sequence fragments into a vertex and transform 119 each fragment that includes a subset of the alleles into an edge.

Processor refers to any device or system of devices that performs processing operations. A processor will generally include a chip, such as a single core or multi-core chip, to provide a central processing unit (CPU). A processor may be provided by a chip from Intel or AMD. A processor may be any suitable processor such as the microprocessor sold under the trademark XEON E7 by Intel (Santa Clara, Calif.) or the microprocessor sold under the trademark OPTERON 6200 by AMD (Sunnyvale, Calif.).

The system uses the processor to create a graph that includes vertices and edges through the use of adjacency lists or index free adjacency. Thus, the processor may create the graph 401 using index-free adjacency wherein a vertex 405 includes a pointer to another vertex 405 to which it is connected and the pointer identifies a physical location in on a memory device where the connected vertex is stored. The graph 401 may be implemented using adjacency lists such that each vertex or edge stores a list of such objects that it is adjacent to. Each adjacency list comprises pointers to specific physical locations within a memory device for the adjacent objects.

A memory device is a mechanical device that stores data or instructions in a machine-readable format. Memory may include one or more sets of instructions (e.g., software) which, when executed by one or more of the processors of the disclosed computers can accomplish some or all of the methods or functions described herein. Preferably, each computer includes a non-transitory memory device such as a solid state drive, flash drive, disk drive, hard drive, subscriber identity module (SIM) card, secure digital card (SD card), micro SD card, or solid-state drive (SSD), optical and magnetic media, others, or a combination thereof.

As used by system 1001, the graph 401 is stored in the memory subsystem that includes one or more memory devices. The memory subsystem may also include phased haplotype information resulting from the performance of method 101 by one or more processors of system 1001. Additionally, system 1001 can be operated to produce a report 901 and provide the report 901 to a user via an input/output device.

An input/output device is a mechanism or system for transferring data into or out of a computer. Exemplary input/output devices include a video display unit (e.g., a liquid crystal display (LCD) or a cathode ray tube (CRT)), a printer, an alphanumeric input device (e.g., a keyboard), a cursor control device (e.g., a mouse), a disk drive unit, a speaker, a touchscreen, an accelerometer, a microphone, a cellular radio frequency antenna, and a network interface device, which can be, for example, a network interface card (NIC), Wi-Fi card, or cellular modem.

Using the described components, the system 1001 is operable to create an edge for each subset of the alleles that are found in one of the fragments, wherein the graph uses pointers to identify a physical location in the memory subsystem where each vertex is stored. The system 1001 preferably determines, for each pair of the plurality of SNPs for which alleles are found in one of the fragments, a best-supported phase for alleles of that pair of SNPs and remove at least one edge from the graph representing a less-supported phase for alleles of that pair of SNPs. In some embodiments, the system 1001 finds a maximum likelihood assignment of each vertex to one or more blocks wherein the probability of the graph given the assignment is optimized, thereby assigning each allele to a haplotype. The system 1001 may then produce a report showing the haplotype for the patient. The system 901 may find the maximum likelihood assignment by (i) initially arbitrarily assigning each vertex to one of the two blocks; (ii) calculating the probability of the graph given the assignment; (iii) making a change to the assignment; (iv) repeating steps (ii) and (iii) to create a chain of assignments; and (v) selecting from the chain the assignment wherein the probability of the graph given that assignment is optimized. Preferably, repeating steps (ii) and (iii) defines a MCMC by modifying the block membership of each vertex in a random fashion and accepting or rejecting the modification according to a change in the probability of the assignment associated with that modification.

In some embodiments, the system 1001 uses sequencer 1055 to obtain the plurality of sequence fragments by sequencing nucleic acid from a sample from the patient. In certain embodiments, the haplotype covers at least 85% of a chromosome of the patient.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for identifying haplotypes in a genome, the method comprising:
    obtaining a plurality of sequence fragments from a genome of an organism;
    transforming, using a processor coupled to a memory subsystem, the sequence fragments into a graph comprising a vertex for each allele of each of a plurality of SNPs found in the plurality of sequence fragments and an edge for each pair of the alleles that are found in one of the fragments;
    for each pair of the plurality of SNPs for which alleles are found in one of the fragments, determine a most-supported phase for alleles of that pair of SNPs and remove any edge from the graph representing a less-supported phase for the alleles of that pair of SNPs; and
    apply a community detection operation to the largest contiguous component of the graph remaining after the edge removal to assign each vertex of that component to a haplotype,
    wherein the haplotype covers at least 85% of a chromosome.

2. The method of claim 1, wherein transforming the sequence fragments into a graph comprises:
    creating the vertices to use index-free adjacency, wherein each vertex includes one pointer for each connected vertex to which that vertex is connected by an edge, wherein each pointer identifies a location of the connected vertex, and
    wherein identifying the location of a connected vertex by a pointer includes identifying a physical location in the memory subsystem where the connected vertex is stored.

3. The method of claim 1, wherein the applying the community detection comprises finding a maximum-likelihood assignment of vertices to one or more blocks, wherein the probability of the graph given the assignment is maximized.

4. The method of claim 3, wherein finding the maximum likelihood assignment includes:
    (i) assigning each node to one of the two blocks;
    (ii) calculating the probability of the graph given the assignment;
    (iii) making a change to the assignment;
    (iv) repeating steps (ii) and (iii) to create a chain of assignments; and
    (v) selecting from the chain the assignment wherein the probability of the graph given that assignment is optimized.

5. The method of claim 4, wherein repeating steps (ii) and (iii) includes modifying the block membership of each vertex in a random fashion and accepting or rejecting the modification according to a change in the probability of the assignment associated with that modification.

6. The method of claim 3, wherein obtaining the plurality of sequence fragments from a genome of an organism comprises sequencing nucleic acid from a sample from the organism.

7. The method of claim 3, wherein the organism is a patient and the plurality of sequence fragments are obtained by sequencing nucleic acid from the patient.

8. The method of claim 7, further comprising producing a report showing the haplotype for the patient.

9. The method of claim 1, wherein each of the plurality of sequence fragments comprises either a sequence read or a pair of paired-end sequence reads.

10. The method of claim 1, wherein at least some of the SNPs correspond to multiple alleles.

11. A method for identifying haplotypes in a genome, the method comprising:
    obtaining a plurality of sequence fragments generated by sequencing nucleic acid from a genome of a patient;
    creating, using a computer system comprising a processor coupled to a memory subsystem, a graph comprising a vertex for each allele of each of a plurality of SNPs found in the plurality of sequence fragments and an edge for each pair of the alleles that are found in one of the fragments, wherein the graph uses pointers to identify a physical location in the memory subsystem where each vertex is stored;
    determining, for each pair of the plurality of SNPs for which alleles are found in one of the fragments, a best-supported phase for alleles of that pair of SNPs and remove at least one edge from the graph representing a less-supported phase for alleles of that pair of SNPs;
    finding a maximum likelihood assignment of vertices to one or more blocks wherein the probability of the graph given the assignment is maximized, thereby assigning each allele to a haplotype; and
    producing a report showing the haplotype for the patient, wherein the haplotype covers at least 85% of a chromosome.

12. The method of claim 11, wherein finding the maximum likelihood assignment includes:
    (i) assigning each vertex to one of the two blocks;
    (ii) calculating the probability of the graph given the assignment;
    (iii) making a change to the assignment;
    (iv) repeating steps (ii) and (iii) to create a chain of assignments; and
    (v) selecting the maximum likelihood assignment from the chain of assignments.

13. The method of claim 12, wherein repeating steps (ii) and (iii) defines a Monte Carlo Markov chain by modifying the block membership of each vertex in a random fashion and accepting or rejecting the modification according to a change in the probability of the assignment associated with that modification.

14. The method of claim 13, wherein obtaining the plurality of sequence fragments includes sequencing nucleic acid from a sample from the patient.

15. The method of claim 13, wherein each of the plurality of sequence fragments comprises either a sequence read or a pair of paired-end sequence reads.

16. A system for identifying haplotypes in a genome, the system comprising a processor coupled to a memory subsystem, wherein the system is operable to:
   obtain a plurality of sequence reads generated by sequencing nucleic acid from a genome of a patient;
   create a graph comprising a vertex for each allele of each of a plurality of SNPs found in the plurality of sequence fragments and an edge for each subset of the alleles that are found in one of the fragments;
   determine, for each pair of the plurality of SNPs for which alleles are found in one of the fragments, a best-supported phase for alleles of that pair of SNPs and remove at least one edge from the graph representing a less-supported phase for alleles of that pair of SNPs;
   find an optimal assignment of vertices to one or more blocks by a community detection operation, thereby assigning each allele to a haplotype; and
produce a report showing the haplotype for the patient, wherein the haplotype covers at least 85% of a chromosome.

17. The system of claim 16, wherein finding the optimal assignment includes:
   (i) assigning each vertex to one of the two blocks;
   (ii) calculating the probability of the graph given the assignment;
   (iii) making a change to the assignment;
   (iv) repeating steps (ii) and (iii) to create a chain of assignments; and
   (v) selecting maximum likelihood assignment from the chain.

18. The system of claim 17, wherein repeating steps (ii) and (iii) defines a Monte Carlo Markov chain by modifying the block membership of each vertex in a random fashion and accepting or rejecting the modification according to a change in the probability of the assignment associated with that modification.

19. The method of claim 10, wherein the graph includes at least two paths each corresponding to a haplotype that itself includes multiple alleles.

20. The method of claim 11, wherein at least some of the SNPs correspond to multiple alleles.

21. The method of claim 20, wherein the graph includes at least two paths each corresponding to a haplotype that itself includes multiple alleles.

22. The system of claim 16, wherein at least some of the SNPs correspond to multiple alleles.

23. The system of claim 22, wherein the graph includes at least two paths each corresponding to a haplotype that itself includes multiple alleles.

* * * * *